US011885733B2

(12) United States Patent
Higgins et al.

(10) Patent No.: US 11,885,733 B2
(45) Date of Patent: Jan. 30, 2024

(54) WHITE BLOOD CELL POPULATION DYNAMICS

(71) Applicant: The General Hospital Corporation, Boston, MA (US)

(72) Inventors: John M. Higgins, Cambridge, MA (US); Anwesha Chaudhury, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/687,270

(22) Filed: Mar. 4, 2022

(65) Prior Publication Data

US 2022/0187190 A1 Jun. 16, 2022

Related U.S. Application Data

(62) Division of application No. 16/091,576, filed as application No. PCT/US2017/026695 on Apr. 7, 2017, now Pat. No. 11,293,852.

(60) Provisional application No. 62/466,590, filed on Mar. 3, 2017, provisional application No. 62/437,468, filed on Dec. 21, 2016, provisional application No. 62/319,370, filed on Apr. 7, 2016.

(51) Int. Cl.
*G01N 15/14* (2006.01)
*G16Z 99/00* (2019.01)
*G01N 33/49* (2006.01)
*G01N 15/00* (2006.01)
*G01N 15/10* (2006.01)

(52) U.S. Cl.
CPC ......... *G01N 15/1459* (2013.01); *G16Z 99/00* (2019.02); *G01N 33/49* (2013.01); *G01N 2015/008* (2013.01); *G01N 2015/1006* (2013.01); *G01N 2015/1402* (2013.01); *G01N 2015/1488* (2013.01); *G01N 2015/1493* (2013.01)

(58) Field of Classification Search
CPC ............... G01N 15/1459; G01N 33/49; G01N 2015/008; G01N 2015/1006; G01N 2015/1402; G01N 2015/1488; G01N 2015/1493; G16Z 99/00
See application file for complete search history.

(56) References Cited

U.S. PATENT DOCUMENTS 5,017,497 A 5/1991 Gerard de Grooth et al.
5,266,269 A 11/1993 Niiyama et al.
(Continued)

FOREIGN PATENT DOCUMENTS

JP 1995-105166 4/1995
JP 1999-326315 11/1999
(Continued)

OTHER PUBLICATIONS

Baron et al., "Single-cell transcriptomics reveal the dynamic of haematopoietic stem cell production in the aorta," Nat Commun, Jun. 2018, 9(1):2517, 15 pages.
(Continued)

*Primary Examiner* — Roy M Punnoose
(74) *Attorney, Agent, or Firm* — Fish & Richardson P.C.

(57) ABSTRACT

Systems and methods for modeling and detecting white blood cell population dynamic for diagnosis and treatment, e.g., of acute coronary syndrome or leukocytosis.

20 Claims, 19 Drawing Sheets

(56) References Cited

U.S. PATENT DOCUMENTS

Figure 1A:
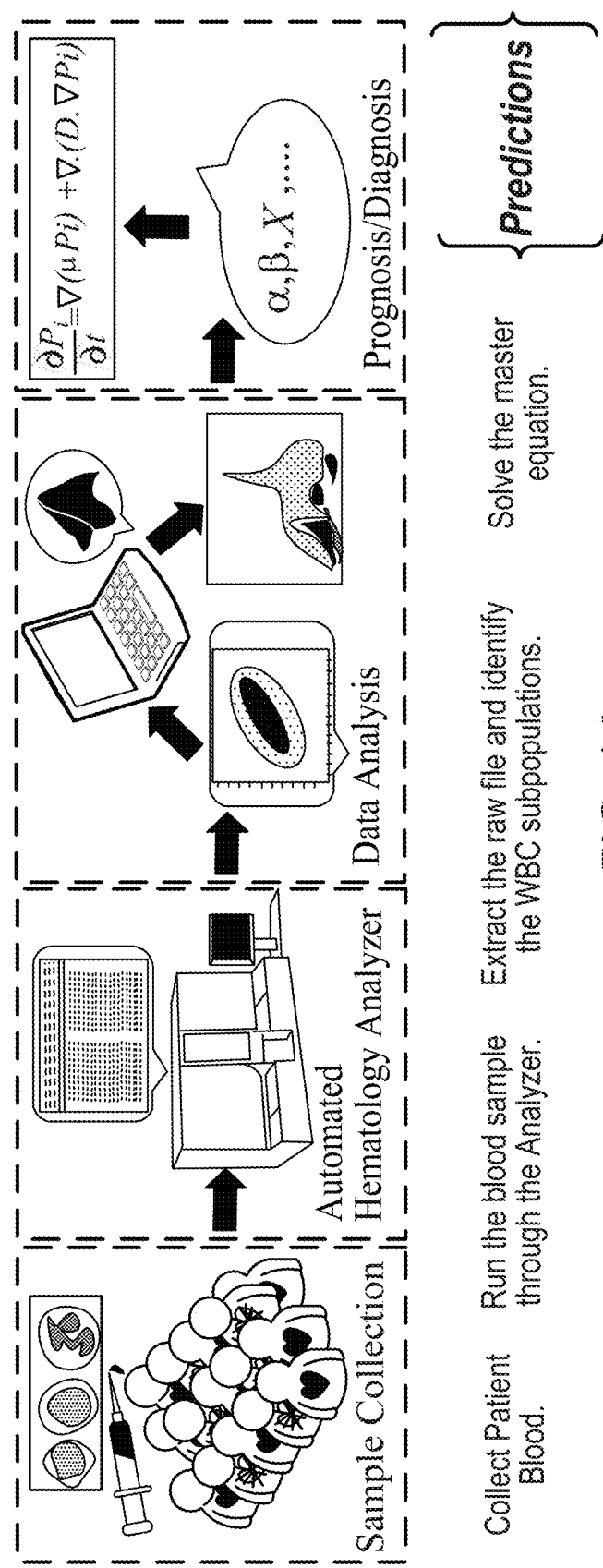
Figure 1B:
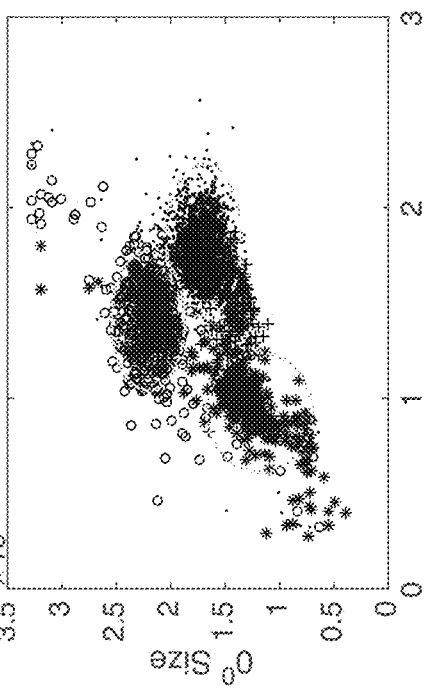
Figure 1C:
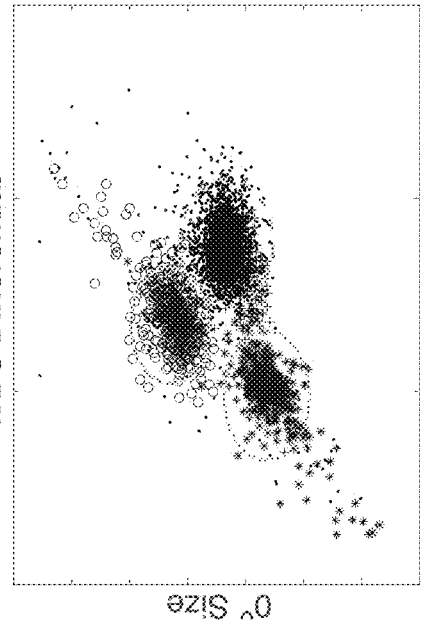
Figure 1D:
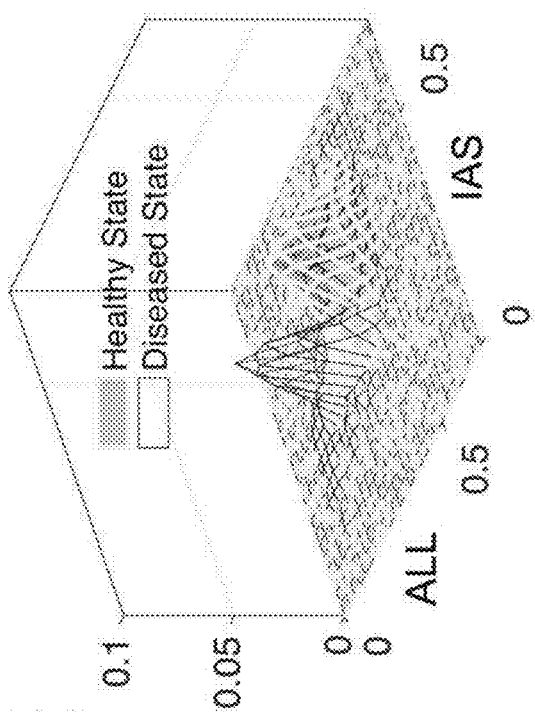
Figure 1D:
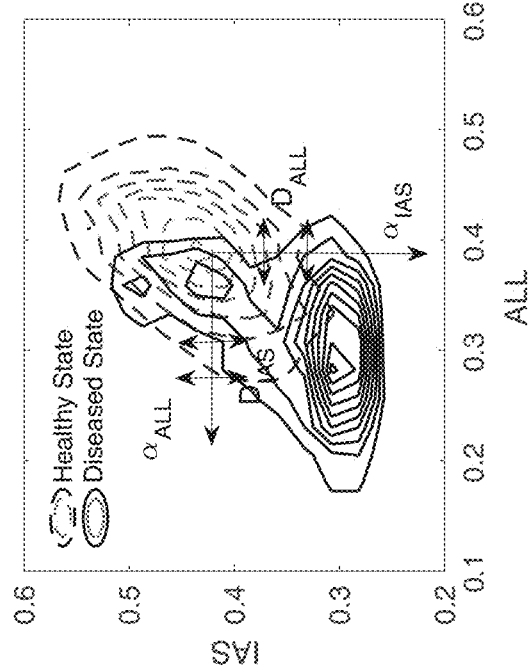

| | | | |
|---|---|---|---|
| 5,369,014 | A | 11/1994 | Brugnara et al. |
| 5,378,633 | A | 1/1995 | von Behrens et al. |
| 5,631,165 | A | 5/1997 | Chupp et al. |
| 5,812,419 | A | 9/1998 | Chupp et al. |
| 5,822,715 | A | 10/1998 | Worthington et al. |
| 6,030,838 | A | 2/2000 | Telmissani |
| 6,228,652 | B1 | 5/2001 | Rodriguez et al. |
| 6,320,656 | B1 | 11/2001 | Ferrante et al. |
| 6,524,858 | B1 | 2/2003 | Zelmanovic et al. |
| 7,324,194 | B2 | 1/2008 | Roche et al. |
| 7,981,681 | B2 | 7/2011 | Champseix et al. |
| 8,481,323 | B2 | 7/2013 | Tyvoll et al. |
| 8,792,693 | B2 | 7/2014 | Satish et al. |
| 10,509,024 | B2 | 12/2019 | Zelmanovic et al. |
| 11,293,852 | B2 | 4/2022 | Higgins et al. |
| 2004/0152199 | A1 | 8/2004 | Kendall et al. |
| 2006/0203226 | A1 | 9/2006 | Roche et al. |
| 2007/0099301 | A1 | 5/2007 | Tyvoll et al. |
| 2007/0172956 | A1 | 7/2007 | Magari et al. |
| 2008/0153170 | A1 | 6/2008 | Garrett et al. |
| 2008/0158561 | A1 | 7/2008 | Vacca et al. |
| 2008/0268494 | A1 | 10/2008 | Linssen |
| 2011/0070210 | A1 | 3/2011 | Andrijauskas |
| 2011/0070606 | A1 | 3/2011 | Winkelman et al. |
| 2011/0077871 | A1 | 3/2011 | Fukuma et al. |
| 2011/0149061 | A1 | 6/2011 | Wardlaw et al. |
| 2011/0164803 | A1 | 7/2011 | Wang et al. |
| 2011/0178716 | A1 | 7/2011 | Krockenberger et al. |
| 2011/0190143 | A1 | 8/2011 | Payen de la Garanderie et al. |
| 2012/0263369 | A1 | 10/2012 | Xie et al. |
| 2013/0236566 | A1 | 9/2013 | Higgins |
| 2014/0030729 | A1* | 1/2014 | Basiji .............. G01N 33/5094 435/6.14 |
| 2014/0187887 | A1 | 7/2014 | Dunn et al. |
| 2015/0160188 | A1 | 6/2015 | Krockenberger et al. |
| 2015/0330963 | A1* | 11/2015 | Vidal .............. G16H 50/20 435/39 |
| 2016/0259884 | A1* | 9/2016 | Han .............. G16B 25/10 |
| 2016/0364544 | A1* | 12/2016 | Das .............. A61B 5/02055 |
| 2017/0108487 | A1 | 4/2017 | Higgins |
| 2017/0228507 | A1 | 8/2017 | Bottinger et al. |
| 2018/0187235 | A1 | 7/2018 | Higgins |
| 2018/0364262 | A1 | 12/2018 | Malka et al. |
| 2019/0066843 | A1 | 2/2019 | Carlson |
| 2019/0113438 | A1 | 4/2019 | Higgins et al. |
| 2019/0336085 | A1* | 11/2019 | Kayser .............. A61B 5/447 |
| 2021/0208167 | A1 | 7/2021 | Malka et al. |
| 2022/0293210 | A1 | 9/2022 | Higgins et al. |

FOREIGN PATENT DOCUMENTS

| | | |
|---|---|---|
| JP | A-2005-503559 | 2/2005 |
| JP | 2006-516735 | 7/2006 |
| JP | 2006-527199 | 11/2006 |
| JP | 2009-36587 | 2/2009 |
| JP | 2009-510402 | 3/2009 |
| JP | 2009-524068 | 6/2009 |
| JP | 2009-524069 | 6/2009 |
| JP | 2010-526873 | 8/2010 |
| WO | WO 2001/077140 | 10/2001 |
| WO | WO 2003/025583 | 3/2003 |
| WO | WO 2004/108121 | 12/2004 |
| WO | WO 2007/0084977 | 7/2007 |
| WO | WO 2011/057744 | 5/2011 |
| WO | WO 2012/037524 | 3/2012 |
| WO | WO 2014/074889 | 5/2014 |
| WO | WO 2021/034770 | 2/2021 |

OTHER PUBLICATIONS

Baumann and Gauldie, "The acute phase response," Immunol Today, Feb. 1994, 15(2):74-80.

Borghans et al., "Current best estimates for the average lifespans of mouse and human leukocytes: reviewing two decades of deuterium-labeling experiments," Immunol Rev, Sep. 2018, 285(1):233-248.

Bosman et al., "Erythrocyte ageing in vivo and in vitro: structural aspects and implications for transfusion," Transfus Med, Dec. 2008, 18(6):335-347.

Bunn, "Erythropoietin," Cold Spring Harb Perspect Med, 2013, 3:a011619, 21 pages.

Cabitza et al., "Unintended consequences of machine learning in medicine," JAMA, Aug. 2017, 318(6):517-518, 2 pages.

CDC.Gov [online], "Clinical Growth Charts," Jun. 16, 2017, retrieved on Jun. 5, 2021, retrieved from URL<https://www.cdc.gov/growthcharts/clinical_charts.htm#Set1>, 5 pages.

Chaturvedi et al., "Evaluation of multiplexed cytokine and inflammation marker measurements: a methodologic study," Cancer Epidemiol Biomarkers Prev, 2011, 20(9):1902-1911.

Chaudhury et al., "Single-cell modeling of routine clinical blood tests reveals transient dynamics of human response to blood loss," eLife, Dec. 2019, 8:e48590, 12 pages.

Chaudhury et al., "White blood cell population dynamics for risk stratification of acute coronary syndrome," Proc Natl Acad Sci, Nov. 2017, 114(46):12344-12349.

Chen and Asch, "Machine learning and prediction in medicine—beyond the peak of inflated expectations," N Engl J Med, Jun. 2017, 376(26):2507-2509.

Dijkstra et al., "Whole blood donation affects the interpretation of hemoglobin A1c," PLOS One, Jan. 2017, 12(1):e0170802, 12 pages.

Dornhorst, "Analytical Review: The Interpretation of Red Cell Survival Curves," Blood, Dec. 1951, 6(12):1284-1292.

Foy et al., "Human acute inflammatory recovery is defined by co-regulatory dynamics of white blood cell and platelet populations," Nat Commun, Aug. 2022, 13(1):4705, 10 pages.

Gabay and Kushner, "Acute-phase proteins and other systemic responses to inflammation," N Engl J Med, Feb. 1999, 340(6):448-454, 8 pages.

Giustacchini et al., "Single-cell transcriptomics uncovers distinct molecular signatures of stem cells in chronic myeloid leukemia," Nat Med, Jun. 2017, 23(6):692-702, 14 pages.

Head et al., "The extent and consequences of p-hacking in science," PLOS Biol, Mar. 2015, 13(3):e1002106, 15 pages.

Hoda et al., "Robbins and Cotran Pathologic Basis of Disease," Am J Clin Pathol, Dec. 2020, 154(6):869.

International Preliminary Report on Patentability in International Appln. No. PCT/US2020/047173, dated Mar. 3, 2022, 9 pages.

International Search Report and Written Opinion in International Appln. No. PCT/US2020/047173, dated Jan. 21, 2021, 12 pages.

Invitation to Pay Additional Fees and, Where Applicable, Protest Fee in International Appln. No. PCT/US2020/047173, mailed on Nov. 3, 2020, 2 pages.

Johnson et al., "Machine learning and decision support in critical care," Proceedings of the IEEE Inst Electr Electron Eng, Feb. 2016, 104(2):444-466.

Khera et al., "Abstract: Measurement of Erythrocyte Survival In Vivo using a Stable Isotope Label in Sickle Cell Anemia," Blood, Nov. 2013, 122(21):2223, 3 pages (Abstract only).

Kim and Ornstein, "Isovolumetric sphering of erythrocytes for more accurate and precise cell volume measurement by flow cytometry," Cytometry, May 1983, 3(6):419-427.

Kotas and Medzhitov, "Homeostasis, inflammation, and disease susceptibility," Cell, Feb. 2015, 160(5):816-827.

Kuczmarski et al., "CDC growth charts: United States," Adv Data, Jun. 2000, 314:1-27, 28 pages.

Leuschner et al., "Rapid monocyte kinetics in acute myocardial infarction are sustained by extramedullary monocytopoiesis," J Exp Med, Jan. 2012, 209(1):123-37.

Liu et al., "Statistical significance of clustering for high-dimension, low-sample size data," J Am Stat Assoc, Sep. 2008, 103(483):1281-1293.

Malka et al., "Mechanistic modeling of hemoglobin glycation and red blood cell kinetics enables personalized diabetes monitoring," Sci Transl Med, Oct. 2016, 8(359):359ra130, 9 pages.

Medzhitov, "Origin and physiological roles of inflammation," Nature, Jul. 2008, 454(7203):428-435.

(56) References Cited

OTHER PUBLICATIONS

Mohandas et al., "Accurate and independent measurement of volume and hemoglobin concentration of individual red cells by laser light scattering," Blood, Aug. 1986, 68(2):506-513.

Obermeyer and Emanuel, "Predicting the future—big data, machine learning, and clinical medicine," N Engl J Med, Sep. 2016, 375(13):1216-9.

O'Brien et al. "The Society of Thoracic Surgeons 2008 Cardiac Surgery Risk Models: Part 2—Isolated Valve Surgery," Ann Thorac Surg, Jul. 2009, 88(1 Suppl):S23-42.

O'Brien et al. "The Society of Thoracic Surgeons 2008 Cardiac Surgery Risk Models: Part 2—Statistical Methods and Results," Ann Thorac Surg, May 2018, 105(5):1419-1428.

Özcan et al., "Red cell distribution width and inflammation in patients with non-dipper hypertension," Blood Press, Apr. 2013, 22(2):80-5.

Pechenizkiy et al., "PCA-based feature transformation for classification: issues in medical diagnostics," Paper, Presented at Proceedings of the IEEE Symposium on Computer-Based Medical Systems, Bethesda, MD, Jun. 23-25, 2004, 6 pages.

Piva et al., "Clinical Utility of Reticulocyte Parameters," Clin Lab Med, 2015, 35:133-163.

Shahian et al., "The Society of Thoracic Surgeons 2008 Cardiac Surgery Risk Models: Part 1—Background, Design Considerations, and Model Development," Ann Thorac Surg, 2018, 105:1411-8.

Shahian et al., "The Society of Thoracic Surgeons 2008 Cardiac Surgery Risk Models: Part 1—Coronary Artery Bypass Grafting Surgery," Ann Thorac Surg, Jul. 2009, 88(1 Suppl):S2-22.

Shalek et al., "Single-cell transcriptomics reveals bimodality in expression and splicing in immune cells," Nature, Jun. 2013, 498(7453):236-40, 13 pages.

Shameer et al., "Machine learning in cardiovascular medicine: Are we there yet?," Heart, Jul. 2018, 104(14):1156-1164.

Shrestha et al., "Models for the red blood cell lifespan," J Pharmacokinet Pharmacodyn., Jun. 2016, 43(3):259-74, 16 pages.

Tibble et al., "Use of surrogate markers of inflammation and Rome criteria to distinguish organic from nonorganic intestinal disease," Gastroenterology, Aug. 2002, 123(2):450-60.

Tusi et al., "Population snapshots predict early haematopoietic and erythroid hierarchies," Nature, Mar. 2018, 555(7694):54-60, 31 pages.

UpToDate.com [online], "Regulation of erythropoiesis," Sep. 2022, retrieved on Oct. 3, 2022, retrieved from URL<https://www.uptodate.com/contents/regulation-of-erythropoiesis#!>, 9 pages.

Wikipedia.org [online], "Hematology analyzer," Jul. 14, 2019, retrieved on Oct. 23, 2020, retrieved from URL<https://en.wikipedia.org/w/index.phptitle=Hematology_analyzer&oldid=906172508>, 3 pages.

[No. Author Listed], "How to read complete blood count," JIM, 2006, 16: 792-795 (with English abstract).

Adams et al., "Cardiac troponin I. A marker with high specificity for cardiac injury," Circulation, 1993, 88: 101-106.

Ali et al., "H2RM: A Hybrid Rough Set Reasoning Model for Prediction and Management of Diabetes Mellitus," Sensors, Jul. 2015, 15: 15921-15951.

Allen et al., "Validation and Potential 10 Mechanisms of Red Cell Distribution Width as a Prognostic Marker in Heart Failure," J Card Fail, Mar. 2010, 16:230-238.

Altenbaugh, "Suitability and Utility of Computational Analysis Tools: characterization of Erythrocyte Parameter Variation," Pacific Symposium on Biocomputing, 2003, 8: 104-115.

American Diabetes Association, "Standards of medical care in diabetes—2010," Diabetes Care, 2010, 33: S11-S61.

Anderson et al., "Usefulness of a complete blood count-derived risk score to predict incident mortality in patients with suspected cardiovascular disease," Am J Cardiol, 2007, 99: 169-174.

Apple et al., "Analytical Characteristics of High-Sensitivity Cardiac Troponin Assays," Clin. Chem, 2011, 58: 54-61.

Athens et al., "Leukokinetic Studies. IV. The Total Blood, Circulating and Marginal Granulocyte Pools and the Granulocyte Turnover Rate in Normal Subjects," J. Clin. Invest, 1961, 40: 989-995.

Bainton et al., "Developmental Biology of Neutrophils and Eosinophils," Inflammation: Basic Principles and Clinical Correlates, Chapter 2, 1999, 13-34.

Barua et al.,, "The relationship between fasting plasma glucose and HbA(1c) during intensive periods of glucose control in antidiabetic therapy," J. Theor. Biol, Dec. 2014, 363: 158-163.

Beach, "A theoretical model to predict the behavior of glycosylated hemoglobin levels," Journal of Theoretical Biology, 1979, 81: 547-561.

Bergman, "Toward Physiological Understanding of Glucose-Tolerance—Minimal-Model Approach," Diabetes, 1989, 38: 1512-1527.

Bergman, et al., "Physiologic Evaluation of Factors Controlling Glucose-Tolerance in Man—Measurement of Insulin Sensitivity and Beta-Cell Glucose Sensitivity from the Response to Intravenous Glucose," Journal of Clinical Investigation, 1981, 68: 1456-1467.

Beutler and Waalen, "The definition of anemia: what is the lower limit of normal of the blood hemoglobin concentration?," Blood, 2006, 107: 1747-1750.

Bunn et al., "The biosynthesis of human hemoglobin A1c. Slow glycosylation of hemoglobin in vivo," Journal of Clinical Investigation, 1976, 57: 1652-1659.

Bunn et al., "The glycosylation of hemoglobin: relevance to diabetes mellitus," Science, Apr. 1978, 200:21-27.

Carstairs, "The Human Small Lymphocyte: Its Possible Pluripotential Quality," Lancet, 1962, 279: 829-832.

Casanova-Acebes et al., "Rhythmic Modulation of the Hematopoietic Niche through Neutrophil Clearance," Cell, 2017, 153: 1025-1035.

Cohen et al., "Red cell life span heterogeneity in hematologically normal people is sufficient to alter HbA1 c," Blood, Nov. 2008, 112:4284-4291.

Cohen et al., "Discordance between HbA(1c) and fructosamine—Evidence for a glycosylation gap and its relation to diabetic nephropathy," Diabetes Care, Jan. 2003, 26: 163-167.

Cohen et al., "Is poor glycemic control associated with reduced red blood cell lifespan?," Diabetes Care, 2004, 27: 1013-1014.

Cook, "Diagnosis and management of iron-deficiency anaemia," Best Practice & Research Clinical Haematology, vol. 18, p. 319-332, 2005.

Cornbleet, "Clinical utility of the band count," Clin. Lab. Med, 2002, 22: 101-136.

Crane et al., "Glucose levels and risk of dementia," New England Journal of Medicine, 2013, 369: 540- 548.

Cronkite and Vincent, "Granulocytopoiesis," Series Haematologica, 1969, II: 3-43.

D'Onofrio et al., "Simultaneous Measurement of Reticulocyte and Red-Blood-Cell Indexes in Healthy- Subjects and Patients with Microcytic Anemia," Blood, 1995, 85(3):818-823.

Damiano et al., "A comparative effectiveness analysis of three continuous glucose monitors: the Navigator, G4 Platinum, and Enlite," Journal of Diabetes Science and Technology, Jul. 2014, 8: 699-708.

Daubert and Jeremias, The utility of troponin measurement to detect myocardial infarction: review of the current findings, Vasc. Health Risk Manag, 2010, 6: 691-699.

DCCT Research Group, "The effect of intensive treatment of diabetes on the development and progression of long-term complications in insulin-dependent diabetes mellitus," N Engl J Med, 1993, 329: 977-986.

De Smet et al., "Use of the Cell-Dyn Sapphire Hematology Analyzer for Automated Counting of Blood Cells in Body Fluids," Am. J. Clin. Pathol, 2010, 133: 291-299.

Eliaz et al., "Modeling failure of metallic glasses due to hydrogen embrittlement in the absence of external loads," Acta Materialia, Jan. 2004, 52: 93-105.

El-Khatib et al., "A Bihormonal Closed-Loop Artificial Pancreas for Type 1 Diabetes," Science Translational Medicine, Apr. 2010, 2: 27ra27, 17 pages.

(56) References Cited

OTHER PUBLICATIONS

Engstrom et al., "Red cell distribution width, haemoglobin A1c and incidence of diabetes mellitus," Journal of Internal Medicine, Aug. 2014, 276: 174-183.
EP Office Action in European U.S. Appl. No. 11/826,059, dated Jan. 29, 2016, 8 pages.
EP Office Action in European Application No. 15803598.0, dated Oct. 16, 2018, 7 pages.
EP Office Action in European U.S. Appl. No. 17/160,801, dated Apr. 2, 2020, 5 pages.
EP Search Report in Application No. 15803598.0, dated Nov. 27, 2017, 10 pages.
EP Search Report in Application No. 17160801.1, dated Jan. 16, 2018, 14 pages.
EP Search Report in Application No. 1716081.1, dated Sep. 25, 2017.
EP Supplementary European Search Report issued in EP 11826059 dated Feb. 21, 2014, 18 pages.
Felker et al., "Red cell distribution width as a novel prognostic marker in heart failure—Data from the CHARM program and the Duke Databank," J Am Coll Cardiol, 2007, 50:40-47.
Franco et al., "Changes in the properties of normal human red blood cells during in vivo aging," Am J Hematol, Jan. 2013, 88:44-51.
Franco, "The measurement and importance of red cell survival," Am J Hematol, Feb. 2009, 84:109-114.
Gardner and Benz Jr., "Anemia of chronic diseases." In: Hoffman et al., eds. Hematology: Basic Principles and Practice. 5th ed. Philadelphia, Pa: Elsevier Churchill Livingstone; 2008:chap 37, 8 pages.
Garner et al., "Genetic influences on F cells and other hematologic variables: a twin heritability study," Blood, 2000, 95(1):342-346.
Georga et al., "Evaluation of short-term predictors of glucose concentration in type 1 diabetes combining feature ranking with regression models," Medical & Biological Engineering & Computing, Dec. 2015, 53: 1305-1318.
George, "Malignant or Benign Leukocytosis," American Society of Hematology, 2012, 475-484.
Gifford et al., "A detailed study of time-dependent changes in human red blood cells: from reticulocyte maturation to erythrocyte senescence," Br J Haematol., 2006, 135(3):395-404.
Gijsberts et al., "Hematological Parameters Improve Prediction of Mortality and Secondary Adverse Events in Coronary Angiography Patients: A Longitudinal Cohort Study," Medicine (Baltimore), Nov. 2015, 94: e1992, 10 pages.
Given et al., "Measurement error in estimated average glucose: a novel approach," Clinical Chemistry and Laboratory Medicine, Jul. 2014, 52: E147-E150.
Golub et al., "Developmental plasticity of red blood cell homeostasis," Am. J. Hematol, May 2014, 89: 459-466.
Gould et al., "Investigation of the mechanism underlying the variability of glycated haemoglobin in non-diabetic subjects not related to glycaemia," Clin. Chim. Acta, Apr. 1997, 260: 49-64.
Gram-Hansen et al., "Glycosylated Hemoglobin (HbA1c) as an Index of the Age of the Erythrocyte Population in NonDiabetic Patients," Eur J Haematol, 1990, 44:201-203.
Harrington et al., "Iron Deficiency Anemia, β-Thalassemia Minor, and Anemia of Chronic Disease: A Morphologic Reappraisal," Am J Clin Pathol., Dec. 2008, 129:466-471.
Hempe et al., "High and low hemoglobin glycation phenotypes in type 1 diabetes: a challenge for interpretation of glycemic control," Journal of Diabetes and Its Complications, 2002, 16: 313-320.
Higgins and Bunn, "Kinetic analysis of the nonenzymatic glycosylation of hemoglobin," Journal of Biological Chemistry, 1981, 256: 5204-5208.
Higgins and Mahadevan, "Physiological and Pathological Population Dynamics of Circulating Human Red Blood Cells," PNAS, Nov. 2010, 107(47):20587-20595.
Hoelzel et al., "IFCC reference system for measurement of hemoglobin A1c in human blood and the national standardization schemes in the United States, Japan, and Sweden: a method-comparison study," Clinical Chemistry, 2004, 50: 166-174.
Hoffstein et al., "Degranulation, membrane addition, and shape change during chemotactic factor-induced aggregation of human neutrophils," J. Cell Biol, 1982, 95: 234-241.
Horne et al., "Which White Blood Cell Subtypes Predict Increased Cardiovascular Risk?," J. Am. Coll. Cardiol, 2005, 45: 1638-1643.
Horne, "A Changing Focus on the Red Cell Distribution Width: Why Does It Predict Mortality and Other Adverse Medical Outcomes?," Cardiology, 2012, 122:213-215.
Horne, "The Red Cell Distribution Width: What Is Its Value for Risk Prognostication and for Understanding Disease Pathophysiology?," Cardiology, 2011, 119:140-141.
Huang et al., "Using Hemoglobin A1C as a Predicting Model for Time Interval from Pre-Diabetes Progressing to Diabetes," Plos One, Aug. 2014, 9(8):e104263, 7 pages.
IDF Diabetes Altas, Seventh Edition, International Diabetes Federation, 2015, 140 pages.
IL Office Action in Israel Application No. 225275, dated Dec. 13, 2015, 7 pages (with English translation).
IL Office Action in Israeli Application No. 225275, dated Jan. 8, 2017, 4 pages, with English translation.
International Preliminary Report on Patentability in International Application No. PCT/US2011/052038, dated Mar. 19, 2013, 7 pages.
International Preliminary Report on Patentability in International Application No. PCT/US2015/034508, dated Dec. 6, 2016, 9 pages.
International Preliminary Report on Patentability in International Application No. PCT/US2016/066860, dated Jun. 9, 2018.
International Preliminary Report on Patentability in International Application No. PCT/US2017/026695, dated Oct. 18, 2018.
International Search Report and Written Opinion in International Application No. PCT/US2016/066860, dated Mar. 2, 2017, 12 pages.
International Search Report and Written Opinion issued in PCT/US2011/052038 dated May 2, 2012, 11 pages.
International Search Report and Written Opinion dated Aug. 27, 2015 in International application No. PCT/US2015/034508, 13 pages.
International Search Report and Written Opinion dated Jun. 27, 2017 in International Application No. PCT/US2017/026695, 18 pgs.
International Search Report and Written Opinion dated Mar. 2, 2017 in international application No. PCT/US2016/066860, 12 pgs.
Jansen et al., "Determinants of HbA1c in nondiabetic Dutch adults: genetic loci and clinical and lifestyle parameters, and their interactions in the lifelines cohort study," Journal of Internal Medicine, 2013, 273:283-293.
Jelkmann and Lundby, "Blood doping and its detection," Blood, Sep. 2011, 118(9):2395-2404.
Jopang et al., "False Positive Rates of Thalassemia Screening in Rural Clinical Setting: 10-Year Experience in Thailand," Southeast Asian J Trop. Med. Public Health, 2009, 40(3):576-580.
JP Office Action in Application No. 2017-144114, dated May 15, 2018, 9 pages (with English translation).
JP Office Action in Japanese Application No. 2015-189343, dated Sep. 6, 2016, 15 pages (with English translation).
JP Office Action issued in JP2013-529382 dated May 26, 2015, 9 pages (with English translation).
Kakkar and Makkar, "Red Cell Cytograms Generated by an AD VIA 120 Automated Hematology Analyzer: Characteristic Patterns in Common Hematological Conditions," Labmedicine, 2009, 40: 549-555.
Kawaguchi et al., "Band neutrophil count and the presence and severity of coronary atherosclerosis," Am. Heart J, 1996, 132: 9-12.
Khera et al., "Use of an oral stable isotope label to confirm variation in red blood cell mean age that influences HbA1c interpretation," Am. J. Hematol, 2015, 90: 50-55.
Kim et al., "Association Between Iron Deficiency and A1C Levels Among Adults Without Diabetes in the National Health and Nutrition Examination Survey, 1999-2006," Diabetes Care, Jan. 2010, 33: 780-785.

(56) References Cited

OTHER PUBLICATIONS

Kitcharoen et al., "A New Screening Program for Thalassemias in Thailand Based on the Complete Blood Count," Medical Online, 1994, 17: 178-183.

Kleophas, "Dose tailoring strategies in haemodialysis patients: a discussion of case histories," Nephrol Dial Transplant, vol. 20 [Suppl 6], p. vi31-vi36, 2005.

Kochanek et al., "Mortality in the United States, 2013," NCHS Data Brief, No. 178. Hyattsville, MD: National Center for Health Statistics, 2014, 8 pages.

Koren-Morag et al., "White blood cell count and the incidence of ischemic stroke in coronary heart disease patients," Am. J. Med, 2005, 118: 1004-1009.

Kovatchev et al., "Accuracy and Robustness of Dynamical Tracking of Average Glycemia (A1c) to Provide Real-Time Estimation of Hemoglobin A1c Using Routine Self-Monitored Blood Glucose Data," Diabetes Technol. Ther, May 2014, 16: 303-309.

Ladyzynski et al., "Hemoglobin Glycation Rate Constant in Non-diabetic Individuals," Ann Biomed Eng, 2011, 39:2721-2734.

Ladyzynski et al., "Validation of hemoglobin glycation models using glycemia monitoring in vivo and culturing of erythrocytes in vitro," Ann Biomed Eng, 2008, 36: 1188-1202.

Lang et al., "Mechanisms of suicidal erythrocyte death," Cell Physiol Biochem., 2005, 15(5):195-202.

Lenters-Westra and Slingerland, "Six of Eight Hemoglobin A(1c) Point-of-Care Instruments Do Not Meet the General Accepted Analytical Performance Criteria," Clinical Chemistry, Jan. 2010, 56: 44-52.

Leslie and Cohen, "Biologic variability in plasma glucose, hemoglobin A1e, and advanced glycation end products associated with diabetes complications," Journal of Diabetes Science and Technology, Jul. 2009, 3:635-643.

Lew et al., "Generation of Normal Human Red-Cell Volume, Hemoglobin Content, and Membrane Area Distributions by "Birth" or Regulation," Blood, 1995, 86(1):334-341.

Lippi et al., "Stability of blood cell counts, hematologic parameters and reticulocytes indexes on the Advia A120 hematologic analyzer," J Lab. Clin. Med., 2005, 146(6):333-340.

Lledó-García et al., "A semi-mechanistic model of the relationship between average glucose and HbA1c in healthy and diabetic subjects." Journal of Pharmacokinetics and Pharmacodynamics, 2013, 14 pages.

Lozoff et al., "Long-Term Developmental Outcome of Infants with Iron-Deficiency," N Engl J Med, Sep. 1991, 325:687-694.

Lundby, "Erythropoietin treatment elevates haemoglobin concentration by increasing red cell volume and depressing plasma volume," J Physiol, 578, Jan. 2007, 309-314.

Mackay, "Homing of naive, memory and effector lymphocytes," Curr. Opin. Immunol, 1993, 5: 423- 427.

Madjid et al., "Leukocyte count and coronary heart disease," J. Am. Coll. Cardiol, 2004, 44: 1945-1956.

Malka et al., "In vivo volume and hemoglobin dynamics of human red blood cells," PLoS Comput. Biol, 2014, 10: e1003839, 12 pages.

Matthews et al., "Homeostasis model assessment: insulin resistance and beta-cell function from fasting plasma glucose and insulin concentrations in man," Diabetologia, Jul. 1985, 28: 412-419.

Menezes et al., "Targeted clinical control of trauma patient coagulation through a thrombin dynamics model," Sci. Transl. Med, 2017, 9: eaaf5045, 11 pages.

Menon et al., "Leukocytosis and adverse hospital outcomes after acute myocardial infarction," Am. J. Cardio1, 2003, 92: 368-372.

Milbrandt et al., "Predicting late anemia in critical illness," Crit. Care, 2006, 10(1), 8 pages.

Mock et al., "Measurement of Posttransfusion Red Cell Survival With the Biotin Label," Transf Med Rev, Jul. 2014, 28: 114-125.

Mortensen et al., "Glucosylation of human haemoglobin a. dynamic variation in HbA 1c described by a biokinetic model," Clinica Chimica Acta, 1984, 136: 75-81.

Mosior et al., "Critical cell volume and shape of bovine erythrocytes," General Physiology and Biophysics, Oct. 1992, 499-506.

Nathan et al., "Translating the A1C assay into estimated average glucose values," Diabetes Care, 2008, 31: 1-6.

Neumann and Nurse, "Nuclear size control in fission yeast," J. Cell Biol, 2007, 179: 593-600.

Ntaios et al., "Discrimination indices as screening tests for beta-thalassemic Trait," Ann. Hematol., 2007, 86(7):487-491.

Office Action in U.S. Appl. No. 13/823,338, dated Apr. 7, 2017, 17 pages.

Osterman-Golkar and Vesper, "Assessment of the relationship between glucose and A1c using kinetic modeling," Journal of Diabetes and its Complications, 2006, 20: 285-294.

Pande et al., "The sweep constant concept in phase coarsening," Metallurgical and Materials Transactions, Sep. 1998, 29: 2395-2398.

Pascual-Figal et al., "Red blood cell distribution width predicts new-onset anemia in heart failure patients," Int J Cardiol, 2012, 160: 196-200.

Patel et al., "Modulation of red blood cell population dynamics is a fundamental homeostatic response to disease : Modulation of red blood cell population dynamics," American Journal of Hematology, May 2015, 90: 422-428.

Patel et al., "Red Blood Cell Distribution Width and the Risk of Death in Middle-aged and Older Adults," Arch Intern Med, Mar. 2009, 169:515-523.

Perlstein et al., "Red Blood Cell Distribution 30 Width and Mortality Risk in a Community-Based Prospective Cohort," Arch Intern Med, Mar. 2009, 169:588-594.

Piva et al., "Automated reticulocyte counting: state of the art and clinical applications in the evaluation of erythropoiesis," Clinical Chemistry and Laboratory Medicine, Oct. 2010, 48: 1369-1380.

Prommer, "Total Hemoglobin Mass—A New Parameter to Detect Blood Doping," Medicine & Science in Sports & Exercise, vol. 40, p. 2112-2118, 2008.

Rockey and Cello, "Evaluation of the Gastrointestinal Tract in Patients With Iron-Deficiency Anemia," New Engl J Med., Dec. 1992, 329(23):1691-1695.

Rohlfing et al., "Biological variation of glycohemoglobin," Clinical Chemistry, Jul. 2002, 48: 1116-11118.

Sacks, "Hemoglobin A1c in diabetes: panacea or pointless?," Diabetes, 2013, 62: 41-43.

Segura et al., "Current strategic approaches for the detection of blood doping practices," Forensic Sci Int., 2011, 42-48.

Sens and Gov, "Force balance and membrane shedding at the red blood-cell surface," Phys Rev Lett., 2007, 98(018102):1-4.

Shiga et al., "Laboratory Diagnosis of Anemia and Related Diseases Using Multivariate Analysis," American Journal of Hematology, 1997, 54: 108-117.

Spell et al., "The value of a complete blood 5 count in predicting cancer of the colon," Cancer Detect Prev, 2004, 28:37-42.

Statland et al., "Evaluation of Biologic Sources of Variation of Leukocyte Counts and Other Hematologic Quantities Using Very Precise Automated Analyzers," Am. J. Clin. Pathol, 1978, 69: 48-54.

Tahara and Shima, "Kinetics of HbA(1c), glycated albumin, and fructosamine and analysis of their weight-functions against preceding plasma-glucose level," Diabetes Care, Apr. 1995, 18: 440-447.

Tamhane et al., "Association Between Admission Neutrophil to Lymphocyte Ratio and Outcomes in Patients With Acute Coronary Syndrome," Am. J. Cardiol, 2008, 102: 653-657.

Thompson et al., "Size-dependent B lymphocyte subpopulations: relationship of cell volume to surface phenotype, cell cycle, proliferative response, and requirements for antibody production to TNP-Ficoll and TNP-BA," J. Immunol, 1984, 133: 2333-2342.

Tzur et al., "Cell Growth and Size Homeostasis in Proliferating Animal Cells," Science, 2009, 325: 167-171.

UK Prospective Diabetes Study (UKPDS) Group, "Intensive blood-glucose control with sulphonylureas or insulin compared with conventional treatment and risk of complications in patients with type 2 diabetes (UKPDS 33)," The Lancet, 1998, 352: 837-853.

Veeranna et al., "The Association of Red Cell Distribution Width with Glycated Hemoglobin among Healthy Adults without Diabetes Mellitus," Cardiology, 2012, 122:129-132.

(56) References Cited

OTHER PUBLICATIONS

Wang et al., "Closed-Loop Control of Artificial Pancreatic beta-Cell in Type 1 Diabetes Mellitus Using Model Predictive Iterative Learning Control," IEEE Trans. Biomed. Eng, Feb. 2010, 57: 211-219.

Wang et al., "Heterogeneity of human blood monocyte: two subpopulations with different sizes, phenotypes and functions," Immunology, 1992, 77: 298-303.

Waugh et al., "Rheologic properties of senescent erythrocytes: loss of surface area and volume with red blood cell age," Blood, 1992, 79(5):1351-1358.

Webster et al., "Sizing up the nucleus: nuclear shape, size and nuclear-envelope assembly," J. Cell Sci, 2009, 122: 1477-1486.

Wilkinson and Grand, "Comparison of amino acid sequence of troponin I from different striated muscles," Nature, 1978, 271: 31-35.

Willekens et al., "Erythrocyte vesiculation: a self-protective mechanism?," Br J Haematol, Apr. 2008, 141:549-556.

Willekens et al., "Hemoglobin loss from erythrocytes in vivo results from spleen-facilitated vesiculation," Blood, 2003, 101(2):747-751.

Willekens et al., "Liver Kupffer cells rapidly remove red blood cell-derived vesicles from the circulation by scavenger receptors," Blood, 2005, 105(5):2141-2145.

Yudkin et al., "Unexplained Variability of Glycated Hemoglobin in Nondiabetic Subjects Not Related to Glycemia," Diabetologia, Apr. 1990, 33: 208-215.

Yunoki et al., "MCH is useful for early diagnosis of thalassemia," 2003, 44: 771 PS-1-169 (with English Abstract).

Zecchin et al., "Jump Neural Network for Real-Time Prediction of Glucose Concentration," in Artificial Neural Networks, 2nd Edition, 2015, 1260: 245-259.

Zenker et al., "From inverse problems in mathematical physiology to quantitative differential diagnoses," PLoS Comput. Biol., 2007, 3(11):2072-2086.

Alashwal et al., "The Application of Unsupervised Clustering Methods to Alzheimer's Disease," Frontiers in Computational Neuroscience, May 2019, 13:31, 9 pages.

Chen et al., "Inflammatory responses and inflammation associated diseases in organs," Oncotarget, Dec. 2017, 9(6):7204-7218.

Fahey et al., "Development and validation of clinical prediction models for mortality, functional outcome and cognitive impairment after stroke: a study protocol," BMJ Open, Aug. 2017, 7(8):e014607, 5 pages.

International Search Report and Written Opinion in International Appln. No. PCT/US2022/072988, dated Sep. 23, 2022, 13 pages.

Lou et al., "Clinical usefulness of measuring red blood cell distribution width in patients with hepatitis B," PLoS One, 2012, 7(5):e37644, 6 pages.

Mori et al., "Protocol for project recovery after cardiac surgery: a single-center cohort study leveraging digital platform to characterise longitudinal patient-reported postoperative recovery patterns," BMJ Open, Sep. 2020, 10(9):e036959, 9 pages.

Santimone et al., "White blood cell count, sex and age are major determinants of heterogeneity of platelet indices in an adult general population: results from the MOLI-SANI project," Haematologica, Aug. 2018, 96(8):1180-8.

Ultsch and Lötsch, "Machine-learned cluster identification in high-dimensional data," J Biomed Inform., Feb. 2017, 66:95-104.

Visweswaran et al., "Patient-Specific Models for Predicting the Outcomes of Patients with Community Acquired Pneumonia," AMIA Annu Symp Proc., 2005, 2005:759-63.

Zhang et al., "Platelet-to-white blood cell ratio: A novel and promising prognostic marker for HBV-associated decompensated cirrhosis," J Clin Lab Anal., Dec. 2020, 34(12):e23556, 6 pages.

* cited by examiner

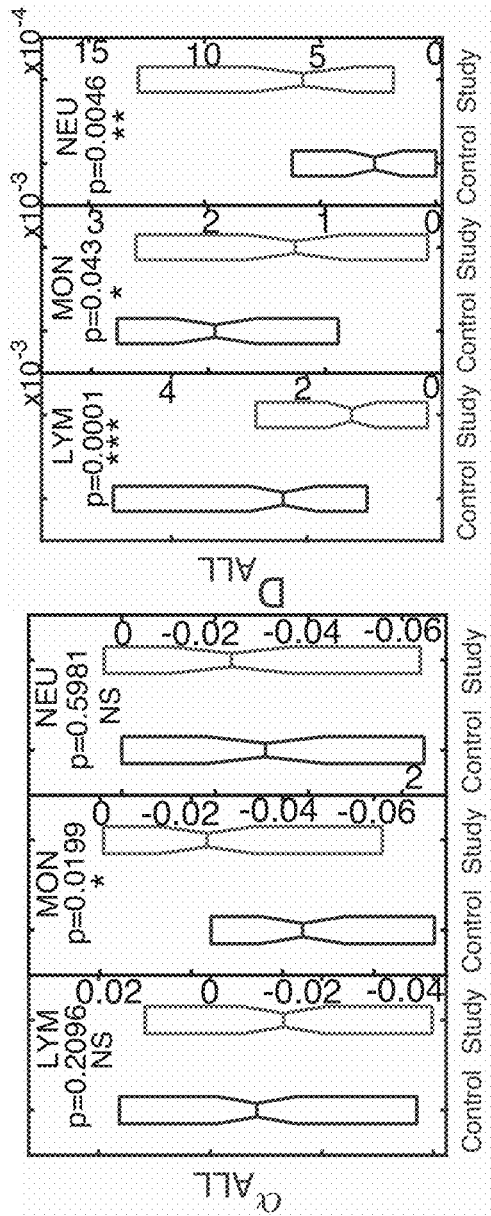
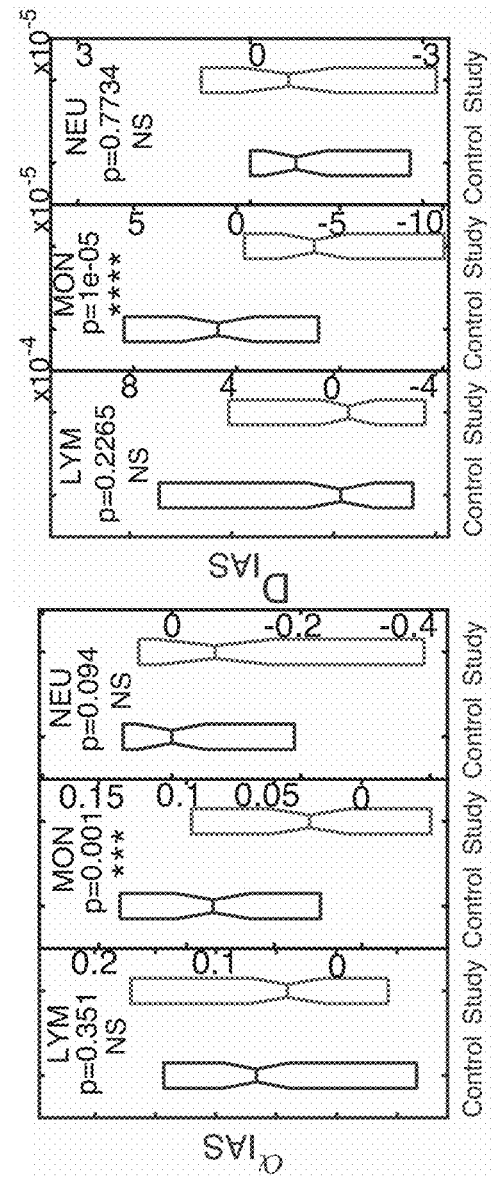
FIG. 2A  FIG. 2B  FIG. 2C  FIG. 2D

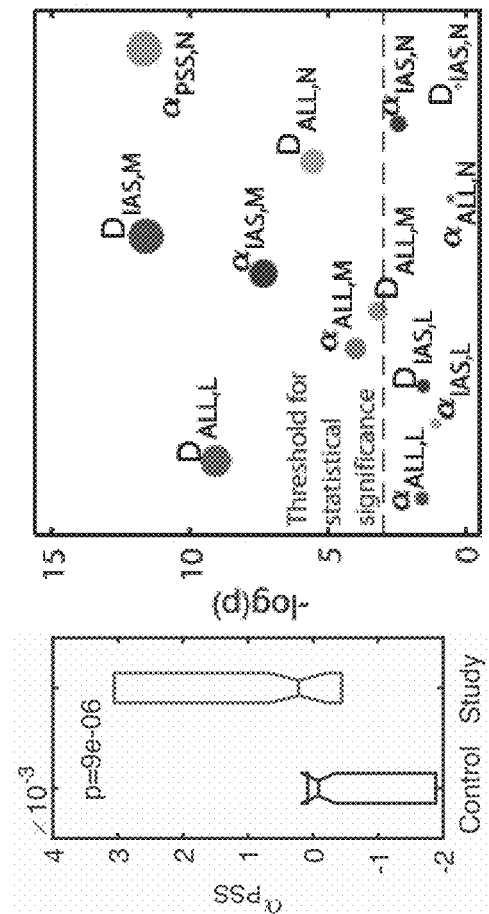
FIG. 2E
FIG. 2F
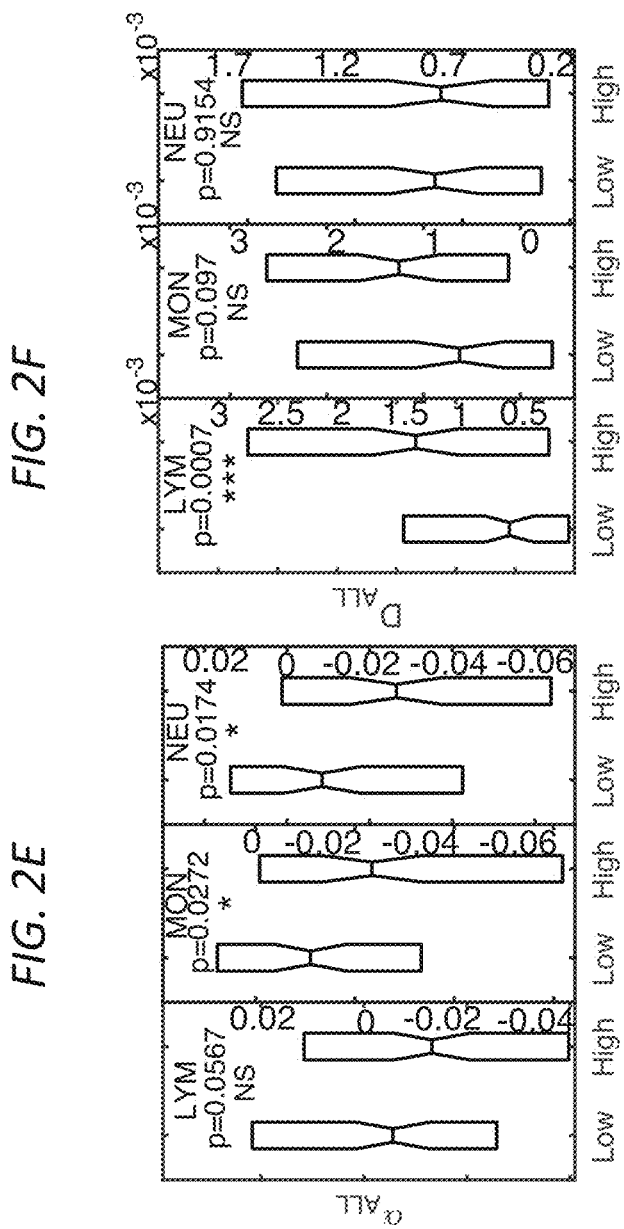
FIG. 3A
FIG. 3B

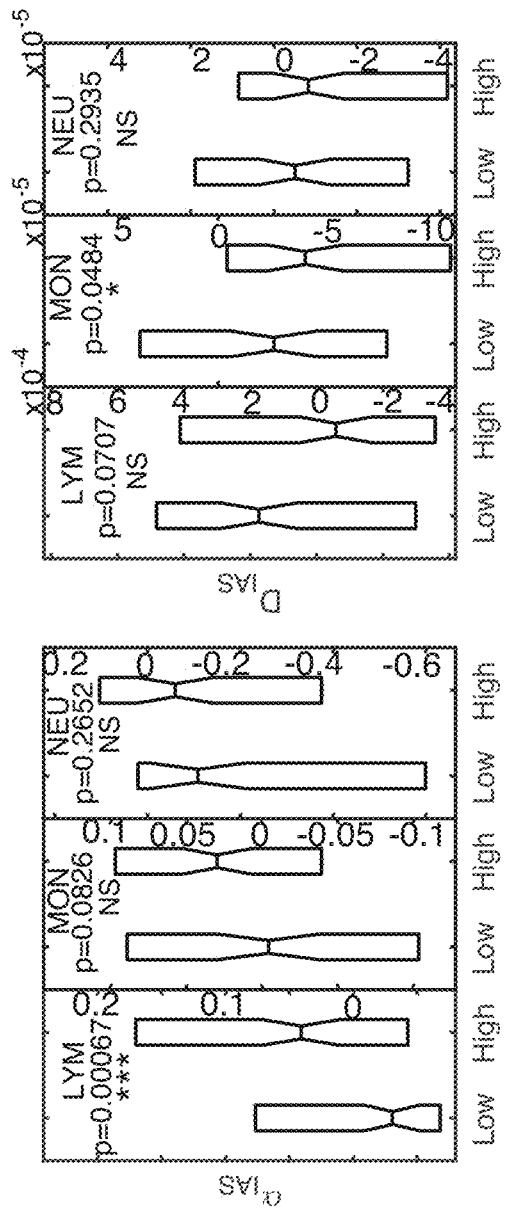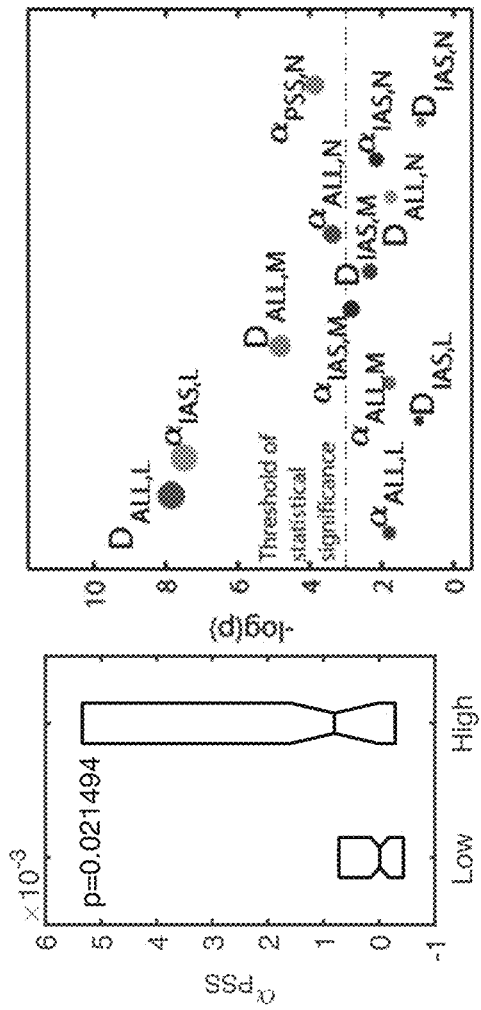

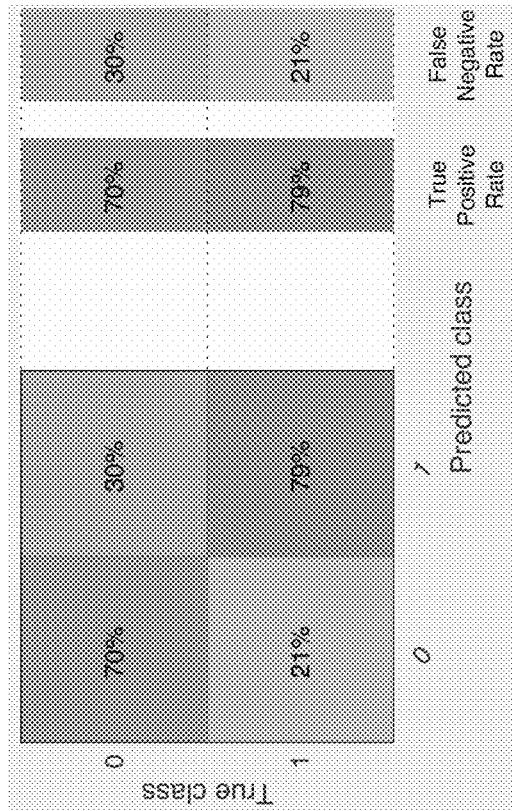
FIG. 4A
FIG. 4B
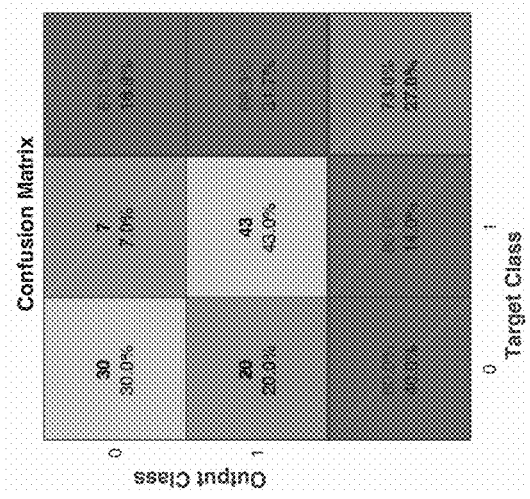
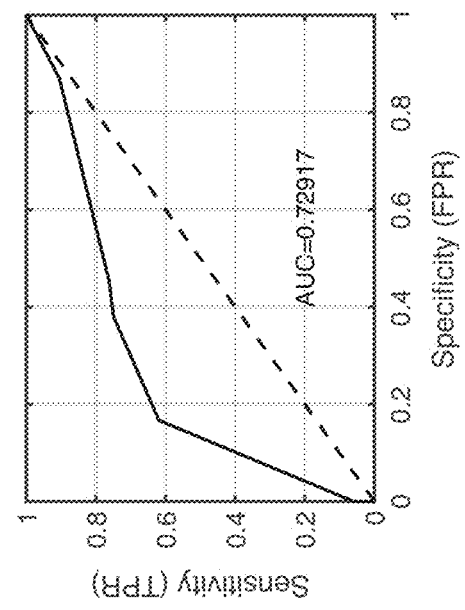
FIG. 4D
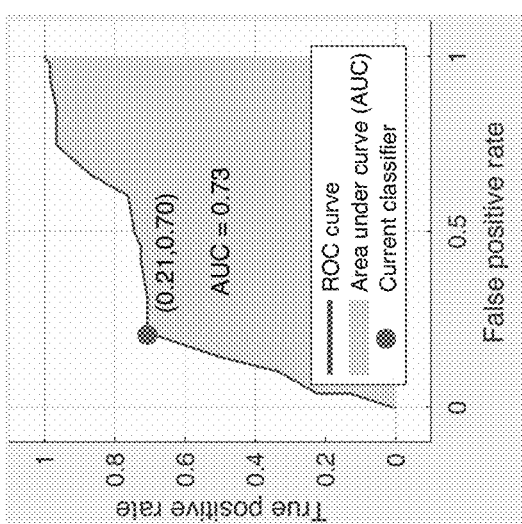
FIG. 4C

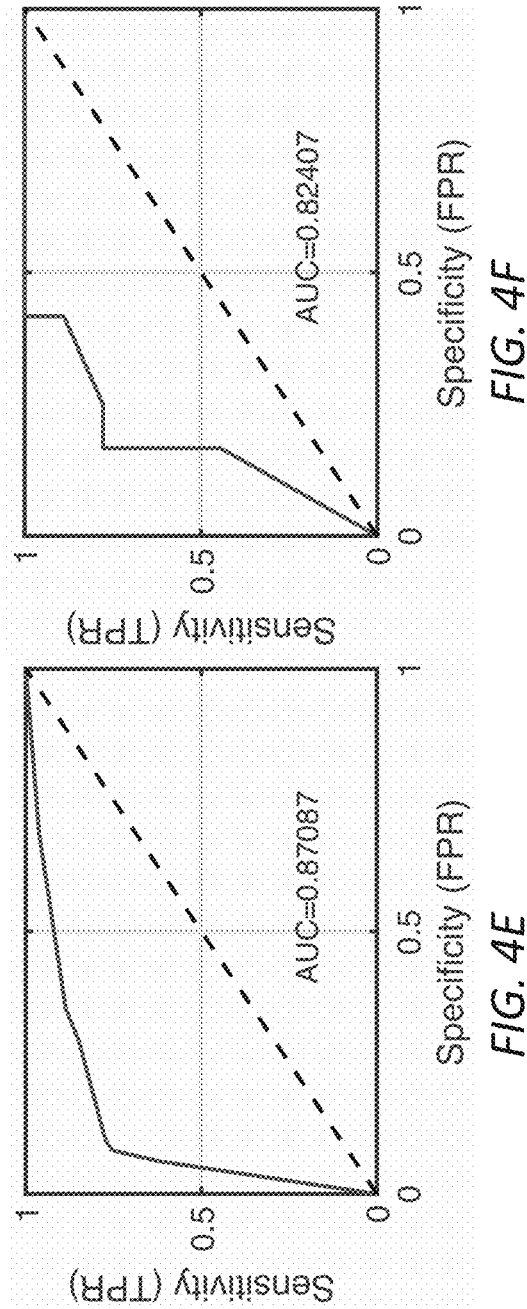
FIG. 4E
FIG. 4F
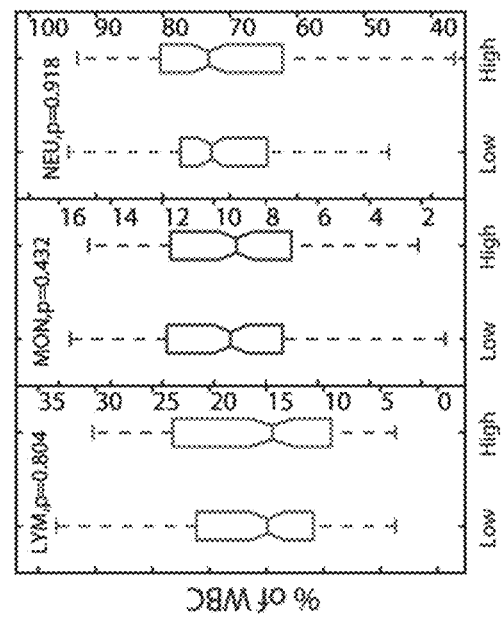
FIG. 5A

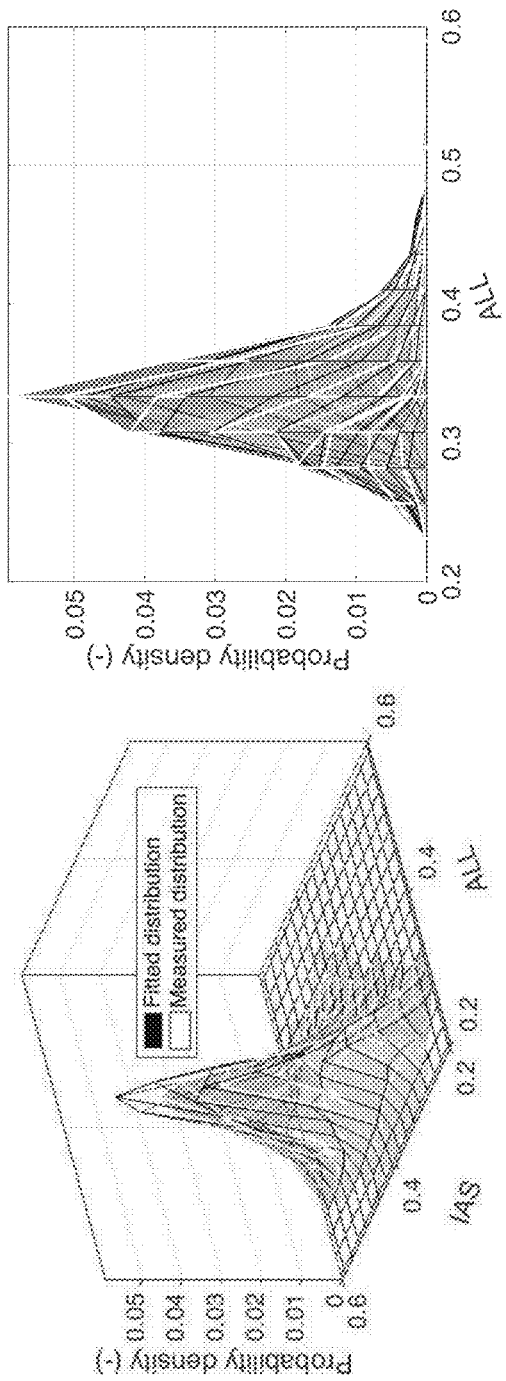
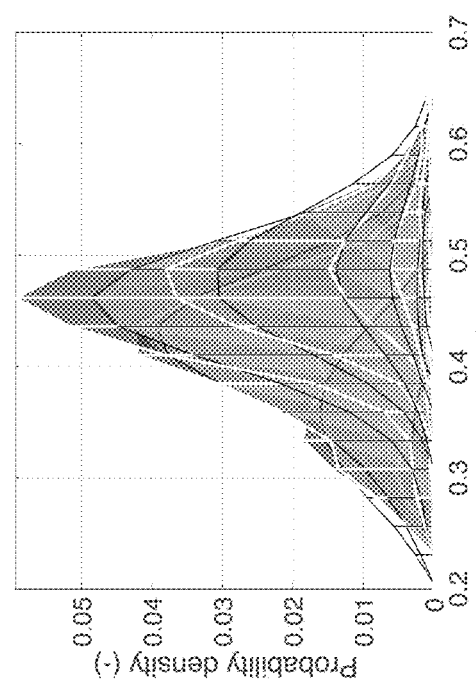
FIG. 6A
FIG. 6B
FIG. 6C

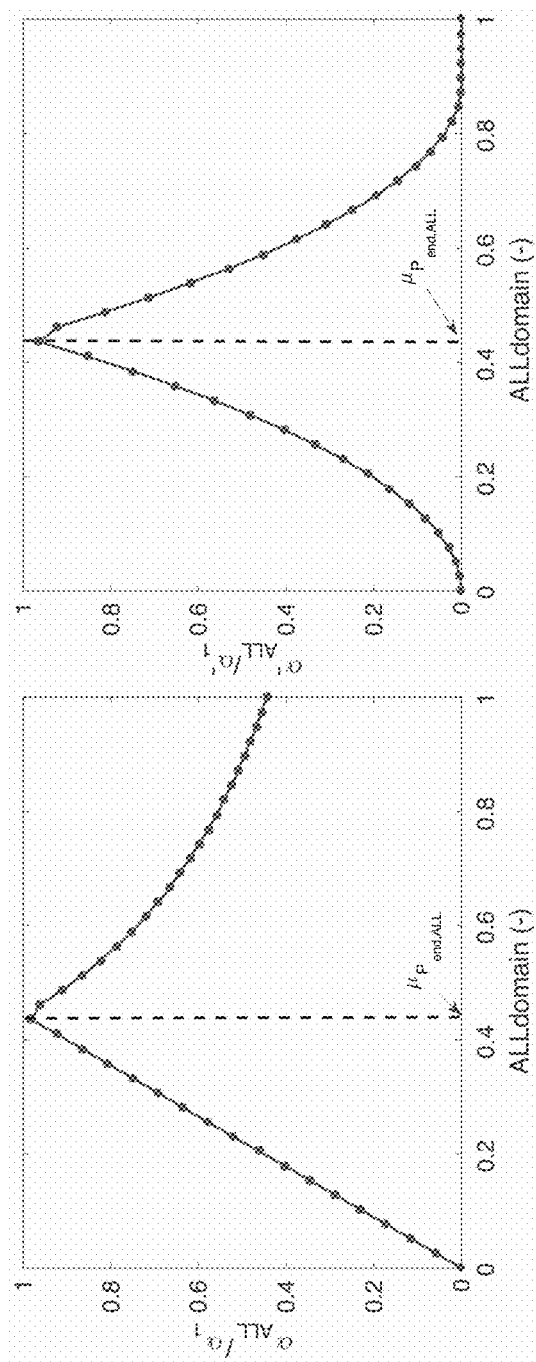
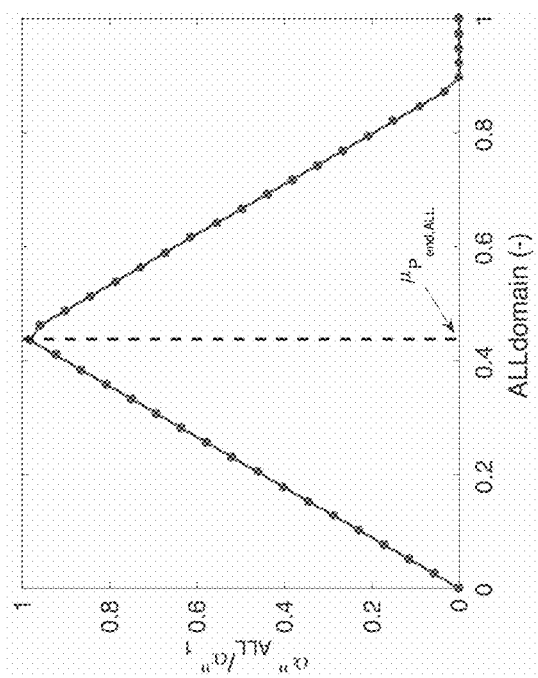
FIG. 7A
FIG. 7B
FIG. 7C

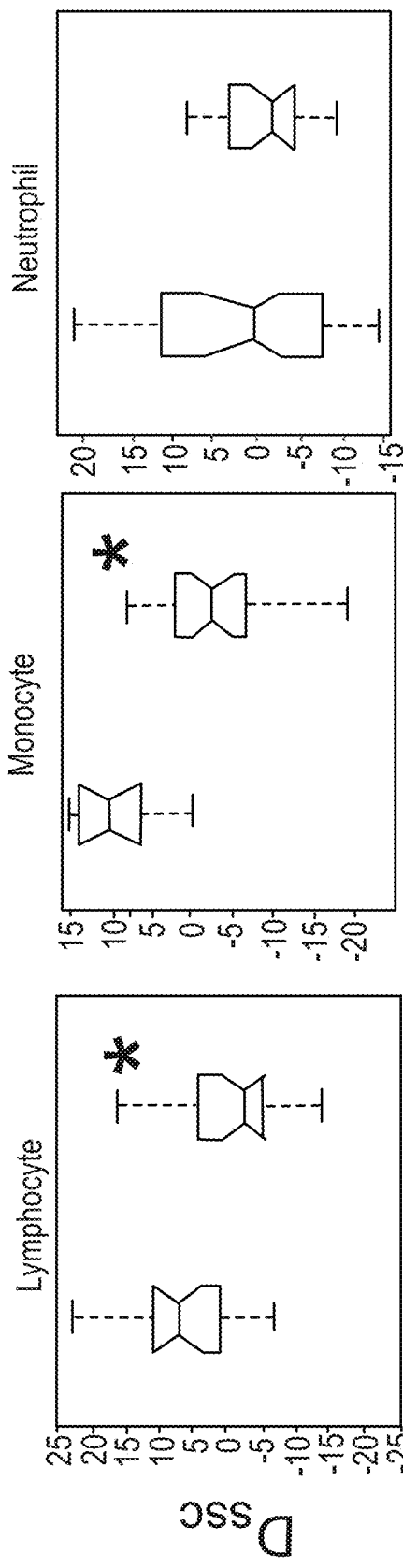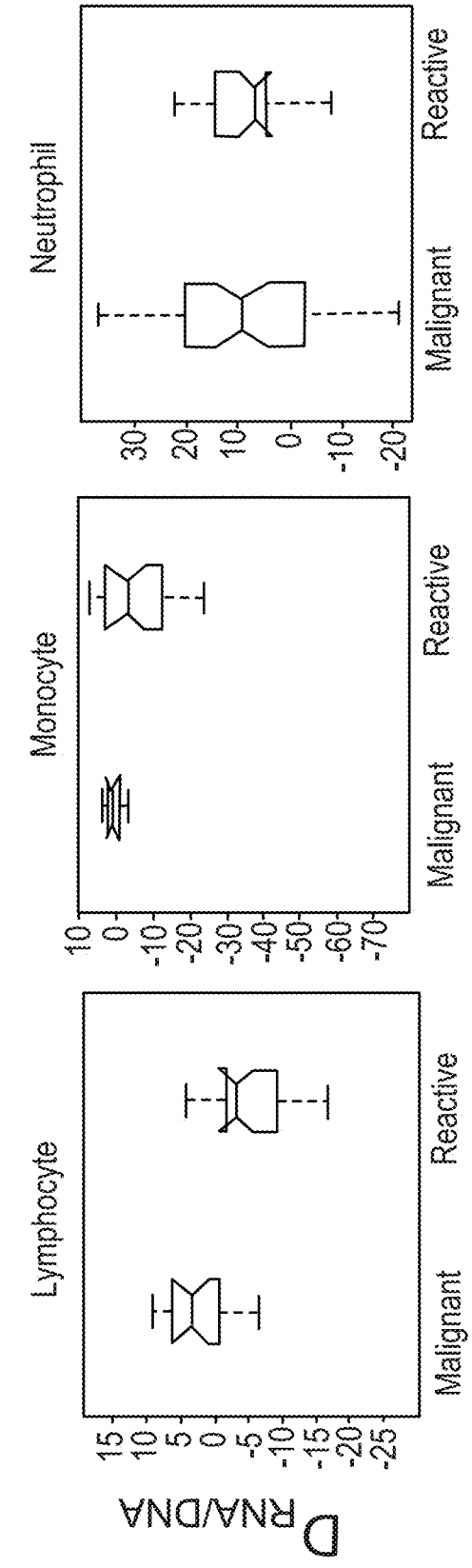
FIG. 10G  FIG. 10H  FIG. 10I
FIG. 10J  FIG. 10K  FIG. 10L

WHITE BLOOD CELL POPULATION DYNAMICS

CLAIM OF PRIORITY

This application is a divisional of U.S. patent application Ser. No. 16/091,576, filed Oct. 5, 2018, which is a § 371 National Stage Application of PCT/US2017/026695, filed on Apr. 7, 2017, which claims the benefit of U.S. Provisional Application Ser. No. 62/319,370, filed on Apr. 7, 2016, U.S. Provisional Application Ser. No. 62/437,468 filed on Dec. 21, 2016, and U.S. Provisional Application Ser. No. 62/466,590 filed on Mar. 3, 2017. The entire contents of the foregoing are incorporated herein by reference.

FEDERALLY SPONSORED RESEARCH OR DEVELOPMENT

This invention was made with Government support under Grant No. DK098087 awarded by the National Institutes of Health. The Government has certain rights in the invention.

TECHNICAL FIELD

Described herein are systems and methods for modeling and detecting white blood cell population dynamic for diagnosis and treatment, e.g., of acute coronary syndrome or leukocytosis.

BACKGROUND

Circulating blood cells continuously interrogate almost all tissues in high throughput, and their collective states of maturation, activation, and proliferation reflect current pathophysiologic states, including healthy quiescence, acute response to pathology, chronic compensation for disease, and ultimately de-compensation. The complete blood count (CBC) reflects these pathophysiologic states. An elevated white blood cell count (WBC) may reflect an ongoing response to infection, hematologic malignancy, or other inflammatory process. The WBC differential reports the fraction of each sub-type of WBC, principally neutrophils, lymphocytes, and monocytes. Patients with high WBC counts may be further classified depending on the predominant WBC subtype for appropriate additional diagnostic testing and patient assessment[1-3].

SUMMARY

Routine complete blood counts (CBC) provide estimates of numbers of currently circulating white blood cells (WBC) and platelets. CBCs also provide current average values for a number of single-WBC and single-platelet characteristics including morphology (e.g., volume) and surface markers (e.g., CD4). WBC counts and platelet counts are important in the diagnosis and management of a wide range of diseases. Current average values of single-WBC and single-platelet characteristics (for instance, neutrophil volume and mean platelet volume) have also been found to correlate strongly with a number of diseases. An understanding of the rates and directions of change in these counts and characteristics would provide earlier and more accurate diagnosis for many conditions.

Provided herein are methods that include receiving data indicative of a property value of each white blood cell (WBC) in a sample of white blood cells (WBCs) of a patient, wherein the data comprises single-cell measurements from a complete blood count; and determining, using parameter estimation, a value indicative of WBC population dynamics of the patient based on the data indicative of the property value of each WBC.

In some embodiments, the data comprises optical, fluorescence, or impedance single-cell measurements from a complete blood count.

In some embodiments, the data is indicative of a morphological property or intracellular composition of each WBC in the sample.

In some embodiments, the data is indicative of cell size, internal complexity, nuclear lobularity, peroxidase content, or DNA/RNA content of each WBC in the sample.

In some embodiments, the data comprise one or more of Axial Light Loss (ALL) representing cell size; Intermediate Angle Scatter (IAS) representing cellular complexity; Polarized Side Scatter (PSS) representing nuclear lobularity; Depolarized Side Scatter (DSS) distinguishing granulocytes (neutrophils and eosinophils); and a fluorescence signal separating nucleated red blood cells, stromal cells and the mononuclear agranulocytes (lymphocytes and monocytes).

In some embodiments, the data are used to determine one or more values selected from the group consisting of $\alpha_{ALL}$, $D_{ALL}$, $\alpha_{IAS}$, $D_{IAS}$, $K_{PSS}$, $\alpha_{SSC,L}$, $\alpha_{SSC,M}$, $\alpha_{RNA/DNA,L}$, $D_{SSC,L}$, $D_{SSC,M}$, and $D_{RBA/DNA,L}$.

In some embodiments, the methods include the one or more values to a reference value. In some embodiments, the reference value represents an identified cohort of subjects, or a value determined at an earlier or later point in time in the same subject.

In some embodiments, the WBCs are selected from the group consisting of neutrophils, lymphocytes, and monocytes.

In some embodiments, the methods include receiving data indicative of a complete blood count of the patient, wherein receiving the data indicative of the complete blood count comprises receiving the data indicative of the property value of each WBC.

In some embodiments, the property value of the parameter is estimated based on data indicative of a predefined normalized property value of WBCs.

In some embodiments, the methods include receiving data indicative of a first complete blood count of the patient in which the property value of each WBC in a first sample of WBCs is measured, and receiving data indicative of a second complete blood count of the patient in which the property value of each WBC in a second sample of WBCs is measured, wherein the value of the parameter is estimated based on the data indicative of the first complete blood count and the data indicative of the second complete blood count.

In some embodiments, the methods include receiving data indicative of a normal template or ensemble of normal complete blood counts in which the property value of each WBC in a first sample of WBCs is measured, and receiving data indicative of a second complete blood count from the patient in which the property value of each WBC in a second sample of WBCs is measured, wherein the value of the parameter is estimated based on the data indicative of the first complete blood count and the data indicative of the second complete blood count.

In some embodiments, the property value is indicative of a property of each WBC selected from the group consisting of cell size, cytoplasmic granularity, morphology, nuclear morphology, and nuclear granularity.

In some embodiments, receiving the data indicative of the property value of each WBC comprises receiving data indicative of axial light loss measurements of the sample of WBCs, intermediate light loss measurements of the sample of WBCs, or polarized side scatter measurements of the sample of WBCs.

In some embodiments, the parameter indicative of the WBC population dynamics of the patient is indicative of a drift or a diffusion of the WBC population dynamics.

In some embodiments, the methods include providing information for treatment or diagnosis of a condition of the patient associated with an inflammatory or immune system response based on the parameter.

In some embodiments, the condition is selected from the group consisting of a hematological malignancy, acute coronary syndrome, urinary tract infection, and an autoimmune disease.

In some embodiments, providing information for treatment or diagnosis of a condition of the patient associated with an inflammatory immune system response based on the parameter comprises providing information for treatment or differential diagnosis of reactive leukocytosis and malignant leukocytosis.

In some embodiments, the troponin level of the patient is within normal range, and or a WBC count is within normal range (e.g., 4,000-11,000 cells/ul blood). The methods can include determining the troponin level of the patient, using known methods.

Also provided herein are systems comprising a processing device, and one or more computer-readable non-transitory media storing instructions that are executable by the processing device, and upon execution cause the processing device to perform a method described herein. For example, the methods can include operations comprising: estimating a value of a parameter indicative of white blood cell (WBC) population dynamics of a patient based on data indicative of a property value of each WBC in a sample of white blood cells (WBCs) of the patient, the property value of a WBC being indicative of an age of the WBC; and optionally providing information for treatment or diagnosis of a condition of the patient associated with an inflammatory or immune system response based on the parameter.

In some embodiments, the WBCs comprise cells selected from the group consisting of neutrophils, lymphocytes, and monocytes.

In some embodiments, the operations include receiving data indicative of a complete blood count of the patient, the data indicative of the complete blood count being indicative of the property value of each WBC.

In some embodiments, the property value of the parameter is estimated based on data indicative of a predefined normalized property value of WBCs.

In some embodiments, the operations further comprise: receiving data indicative of a first complete blood count of the patient in which the property value of each WBC in a first sample of WBCs is measured, and receiving data indicative of a second complete blood count of the patient in which the property value of each WBC in a second sample of WBCs is measured, wherein the value of the parameter is estimated based on the data indicative of the first complete blood count and the data indicative of the second complete blood count.

In some embodiments, the operations further comprise: receiving data indicative of a normal template or ensemble of normal complete blood counts in which the property value of each WBC in a first sample of WBCs is measured, and receiving data indicative of a second complete blood count of the patient in which the property value of each WBC in a second sample of WBCs is measured, wherein the value of the parameter is estimated based on the data indicative of the first complete blood count and the data indicative of the second complete blood count.

In some embodiments, the property value is indicative of a property of each WBC selected from the group consisting of cell size, cytoplasmic granularity, morphology, nuclear morphology, and nuclear granularity.

In some embodiments, receiving the data indicative of the property value of each WBC comprises receiving data indicative of axial light loss measurements of the sample of WBCs, intermediate light loss measurements of the sample of WBCs, or polarized side scatter measurements of the sample of WBCs.

In some embodiments, the parameter indicative of the WBC population dynamics of the patient is indicative of a drift or a diffusion of the WBC population dynamics.

In some embodiments, the parameter is selected from the group consisting of $\alpha_{ALL}$, $D_{ALL}$, $\alpha_{IAS}$, $D_{IAS}$, $K_{PSS}$, $\alpha_{SSC,L}$, $\alpha_{SSC,M}$, $\alpha_{RNA/DNA,L}$, $D_{SSC,L}$, $D_{SSC,M}$, and $D_{RBA/DNA,L}$.

In some embodiments, the condition is selected from the group consisting of a hematological malignancy, acute coronary syndrome, urinary tract infection, and an autoimmune disease.

In some embodiments, providing information for treatment or diagnosis of a condition of the patient associated with an inflammatory immune system response based on the parameter comprises providing information for treatment or differential diagnosis of reactive leukocytosis and malignant leukocytosis.

In some embodiments, a troponin level of the patient is within the normal range (e.g., normal <0.03 ng/ml, abnormal >0.09 ng/ml, and indeterminate in between), and or a WBC count is within normal range.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS (FIGS. 1-9 show results with data collected on an Abbott hematology analyzer.)

FIGS. 1A-D. (A) Schematic showing the analytic workflow. (B) Patient specific scatter plot showing the optical measurements, as measured by the Abbott CELL-DYN Sapphire instrument with the intermediate-angle scatter intensity (IAS) and the axial light-loss intensity (ALL), with B at healthy state and (C) at the time of an elevated Troponin measurement. (D) Probability distribution for the lymphocyte population at the healthy and diseased state, contour plot shows how the model captures the trajectory of the probability distribution for a WBC subpopulation based on drift and diffusion, as the blood cell populations are perturbed or altered in response to a pathologic condition.

FIGS. 2A-F. (A-E) Comparison of the different model parameters for acutely ill patients (Study) and healthy individuals (Control). Parameter estimation for each patient required a CBC at two different time points but can also be done with a normal template (e.g., a set of reference levels determined using data from a defined cohort of subjects, e.g., normal/healthy or disease reference subjects) as a starting point. Study and Control patients had normal WBC counts (4,000-11,000 cells/ul) at both time points (E) This panel shows the log-transformed p values (−log(p)) for the model parameters (subscript L is for lymphocytes ($n_{low}$=123, $n_{high}$=141), M for monocytes ($n_{low}$=88, $n_{high}$=71), and N for neutrophils ($n_{low}$=62, $n_{high}$=64)). Points above the dashed line (−log(0.05)) are significant. The number of observations differs in each cohort due to the exclusion of unsatisfactory parameter fits. These results demonstrate that the model can, in general, distinguish patients with acute illnesses from those who are healthy, even when the two groups are not distinguishable based on WBC counts alone.

FIGS. 3A-F. Comparison of the model parameters for patients who have two normal (low) Troponin measurements versus patients whose Troponin is initially normal and subsequently elevated. Because absolute WBC count has already been shown to correlate with Troponin level and risk of acute coronary syndrome (ACS), we matched WBC counts such that they differed by less than 500/ul at both time points in order to focus on changes in WBC dynamics independent of absolute WBC count. Low Tn-T group (Low Tn-T), Increasing Tn-T (High Tn-T) group, (A) $\alpha_{ALL}$, (B) $D_{ALL}$, (C) $\alpha_{IAS}$, (D) $D_{IAS}$. (E) $K_{PSS}$ pertains to the Neutrophil population only. (F) Showing the transformed p values (−log(p)) for the model parameters (subscript L is for lymphocytes ($n_{low}$=143, $n_{high}$=183), M for monocytes ($n_{low}$=106, $n_{high}$=137), and N for neutrophils ($n_{low}$=115, $n_{high}$=137)). Points above the dashed line (−log(0.05)) are significant.

FIGS. 4A-F. Predicting which patients with normal Troponin will have an elevated Troponin at some point in the subsequent 48 hours. ROC curves for cross-validated decision tree classifiers using the significant model parameters are shown. The dashed line corresponds to an area under the curve (AUC) of 0.5, which indicates no predictive ability of the classifier. The parameters considered in the classifier are lymphocyte $D_{ALL}$, $\alpha_{IAS}$; neutrophil $\alpha_{ALL}$, $K_{PSS}$; and monocyte $D_{ALL}$. (A) Receiver operating characteristic (ROC) curve for the decision tree classifier developed with the training data set under five-fold cross-validation. (B) Confusion matrix showing the performance of the cross-validated decision tree on the training set. (C) ROC curve for the same cross-validated decision tree applied to an independent validation set and showing a similar AUC as expected for cross-validation ($n_{low}$=50, $n_{high}$=50). (D) Confusion matrix showing the performance of the cross-validated trained classifier on the validation set. (E) ROC curve for a decision tree classifier trained for the full training data set without cross-validation. (F) ROC curve for the non cross-validated classifier applied to an independent data set.

Figure 5B:
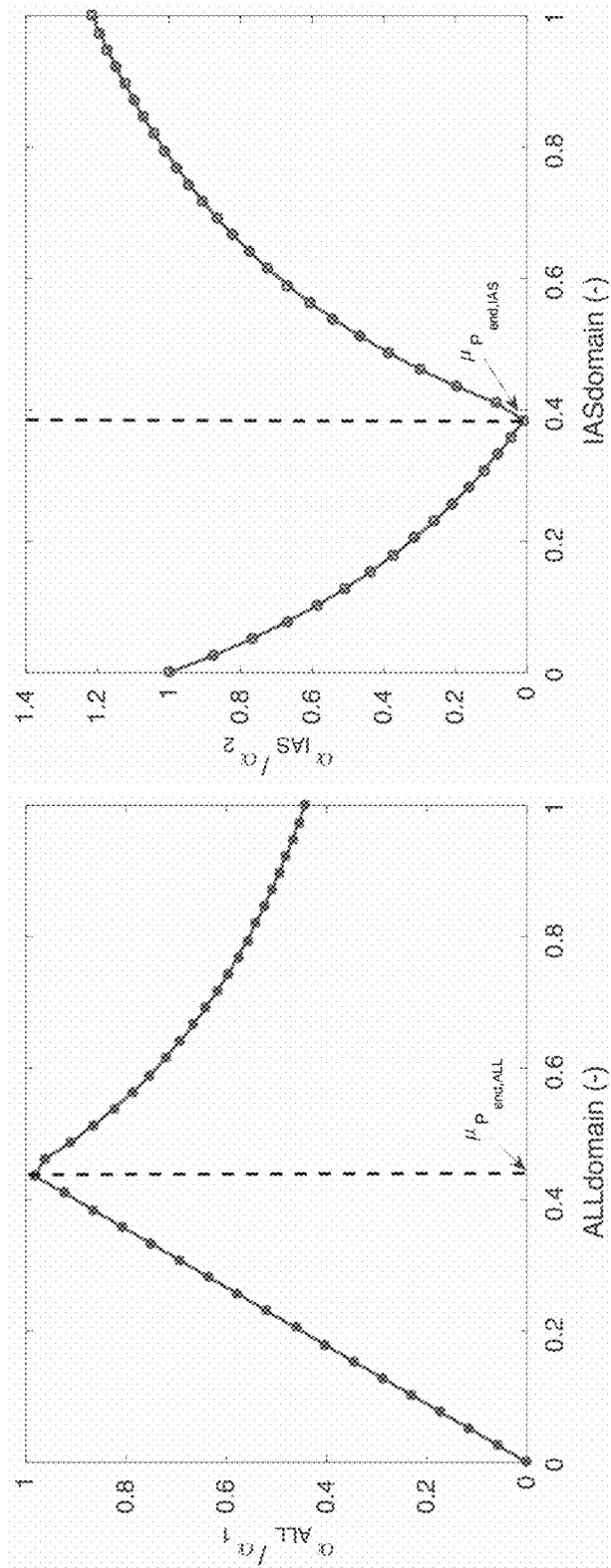
Figure 8A:
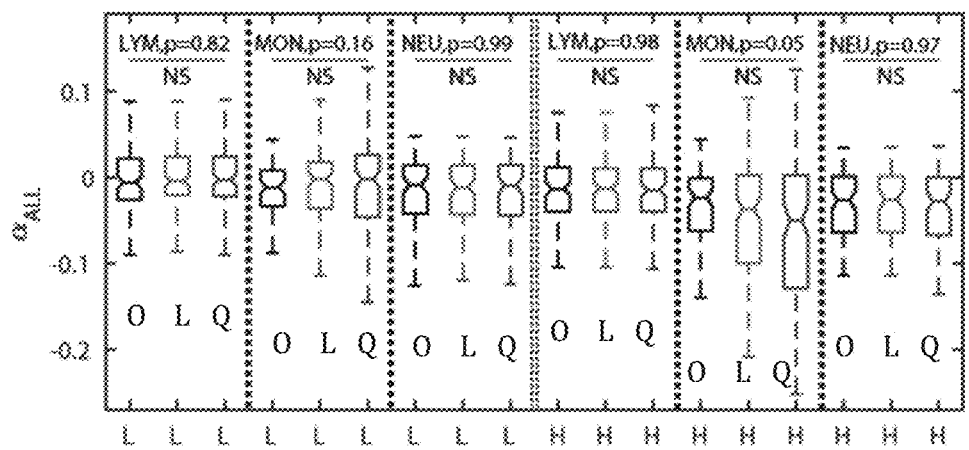
Figure 8B:
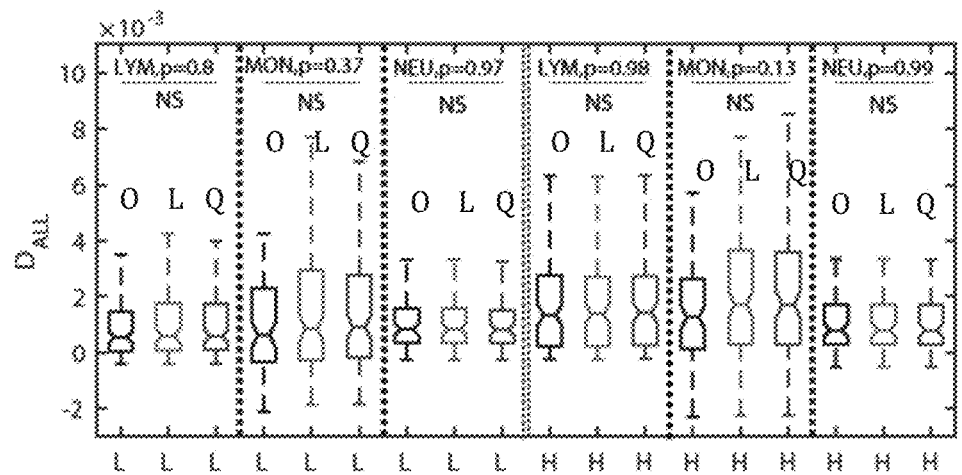
Figure 8C:
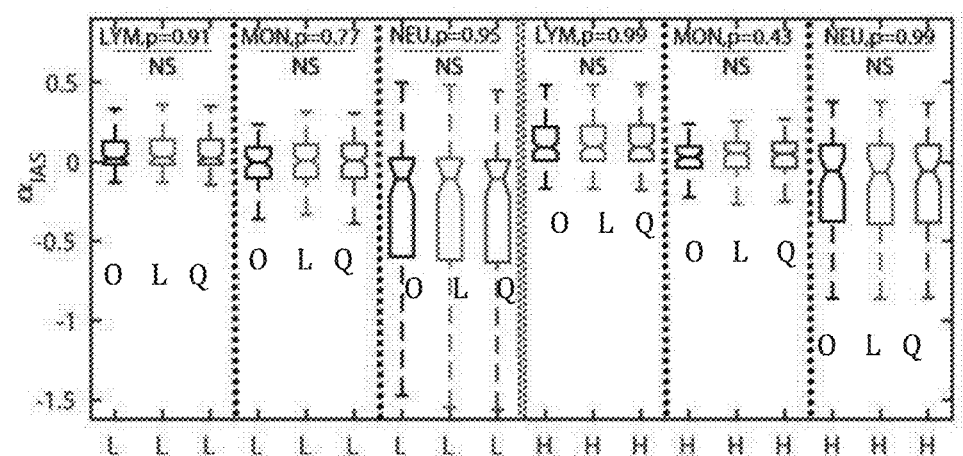
Figure 8D:
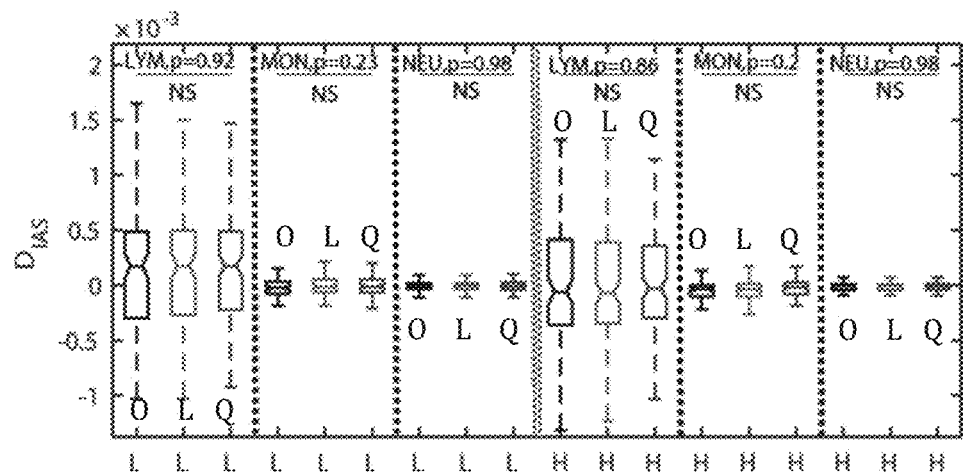
Figure 8E:
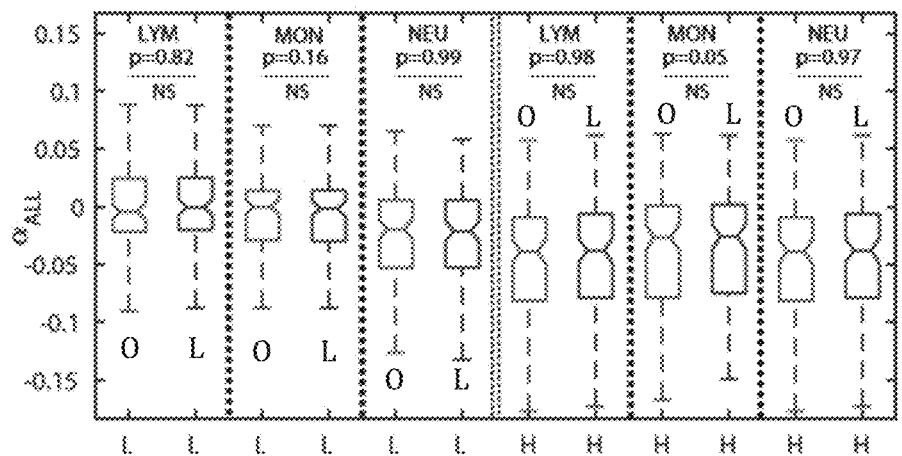
Figure 8F:
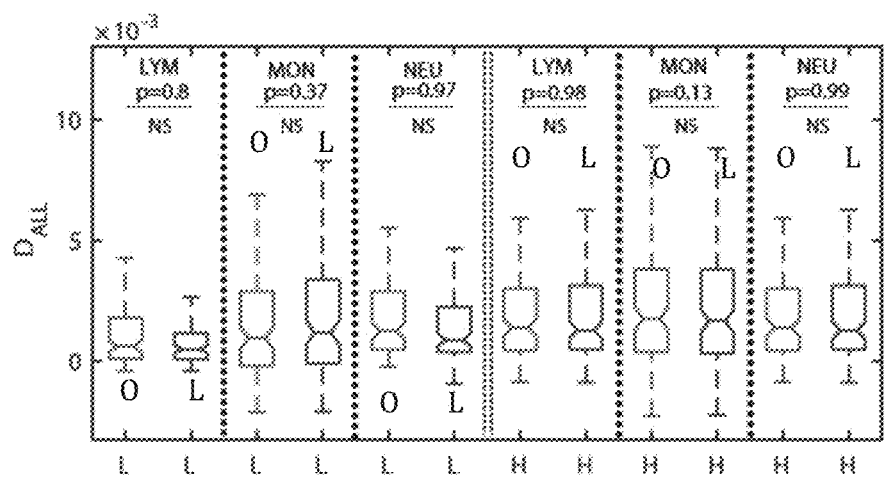
Figure 8G:
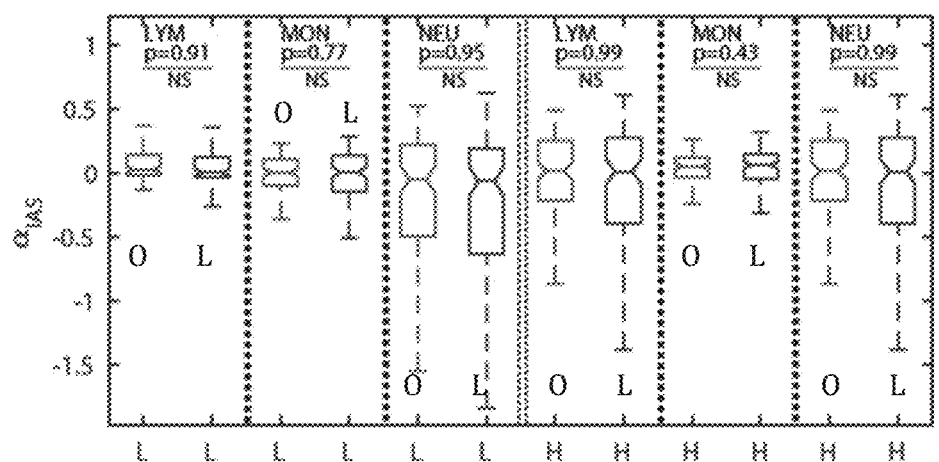
Figure 8H:
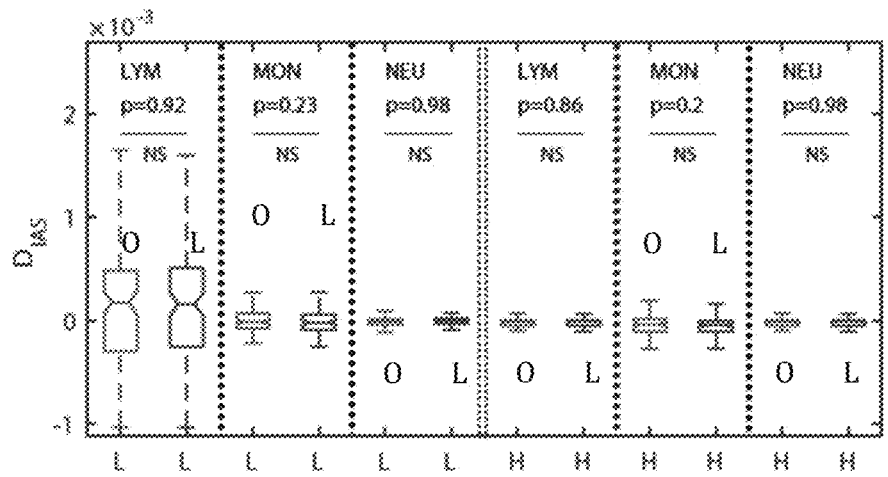
Figure 9A:
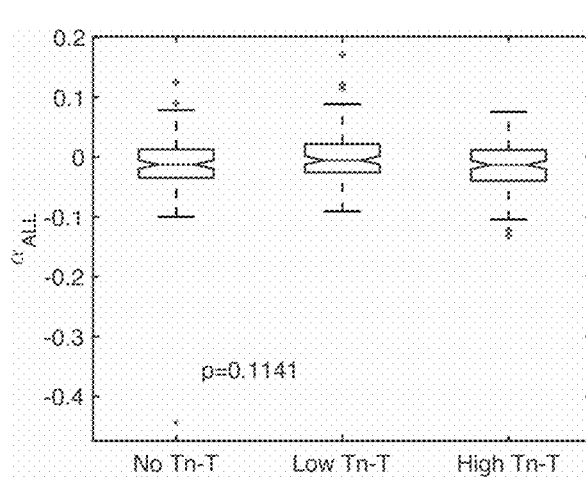
Figure 9B:
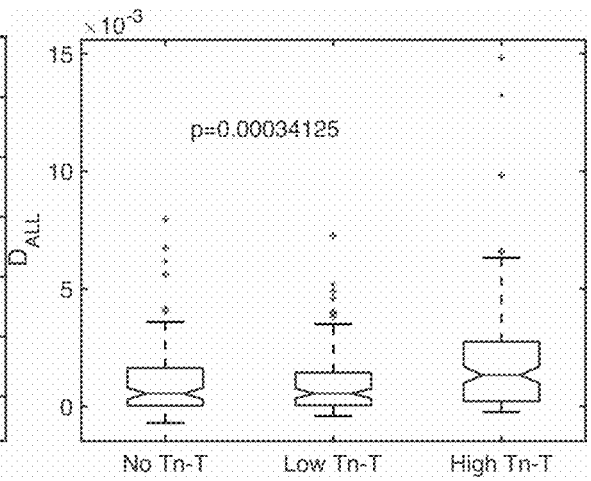
Figure 9C:
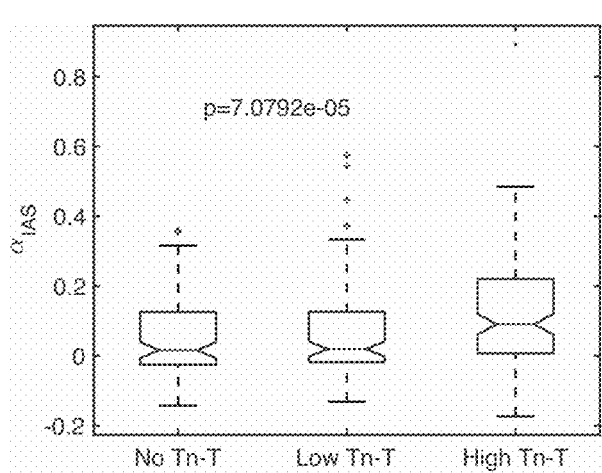
Figure 9D:
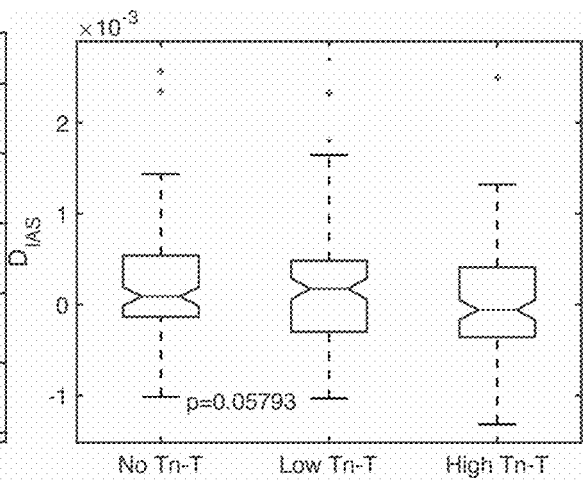
Figure 9E:
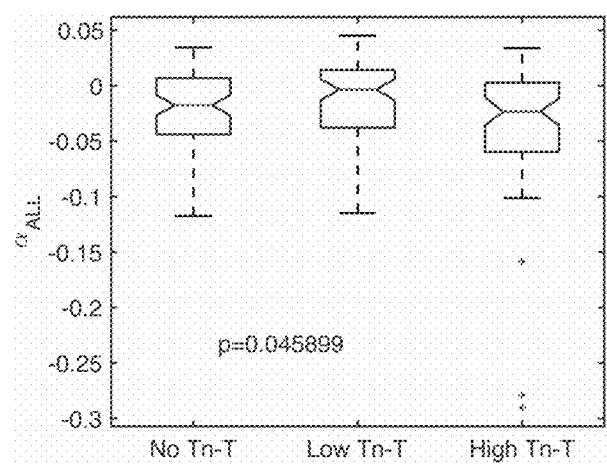
Figure 9F:
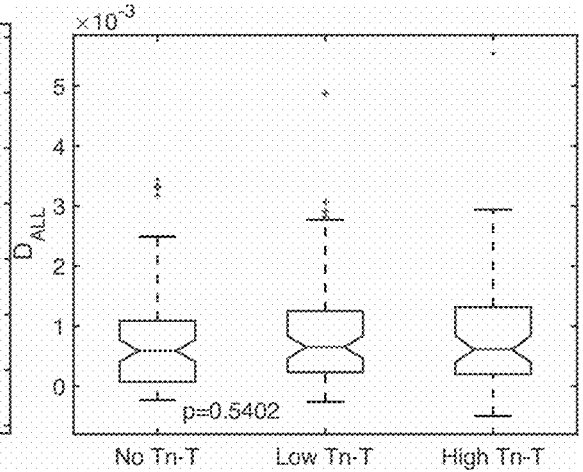
Figure 9G:
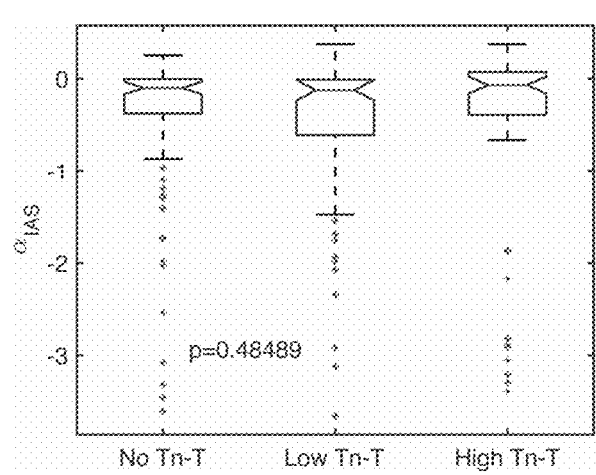
Figure 9H:
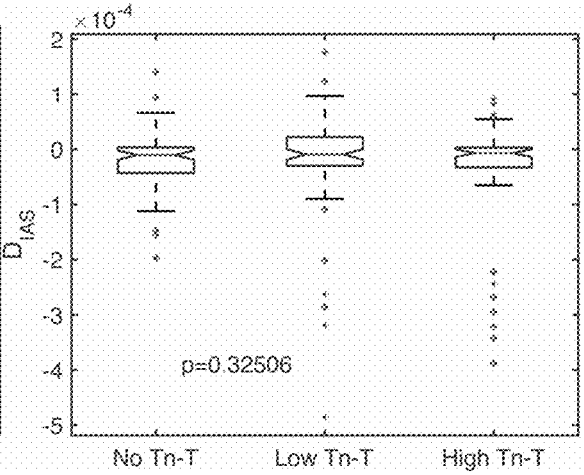
Figure 9I:
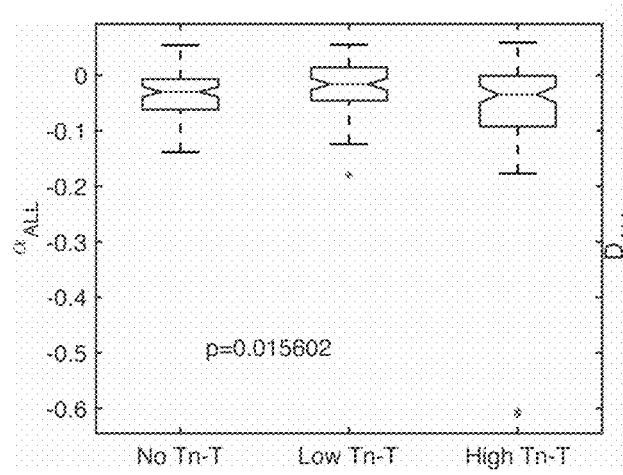
Figure 9J:
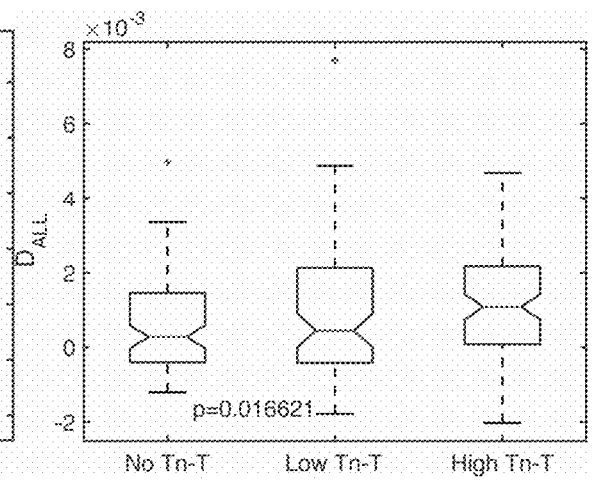
Figure 9K:
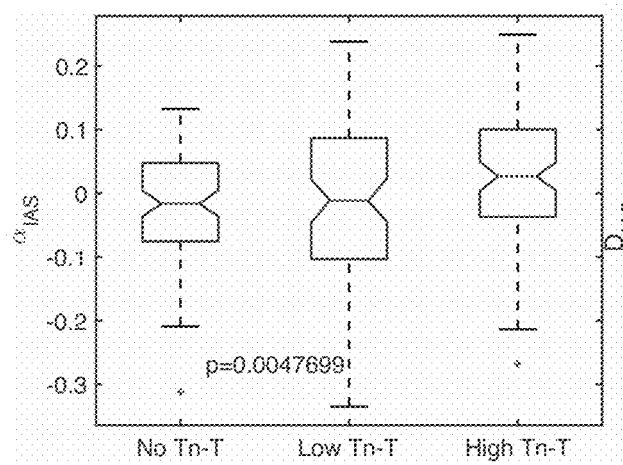
Figure 9L:
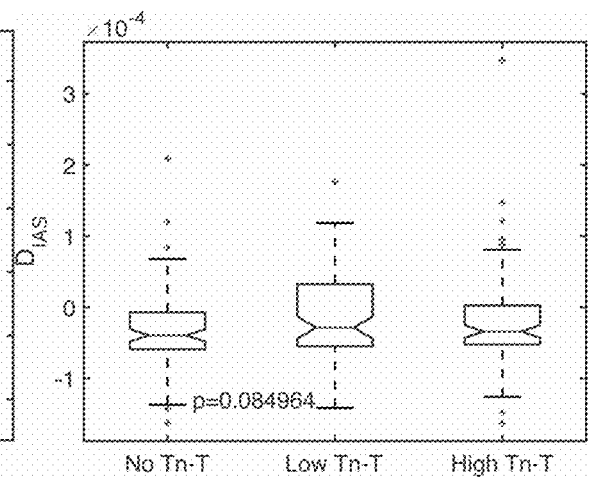
Figure 10A:
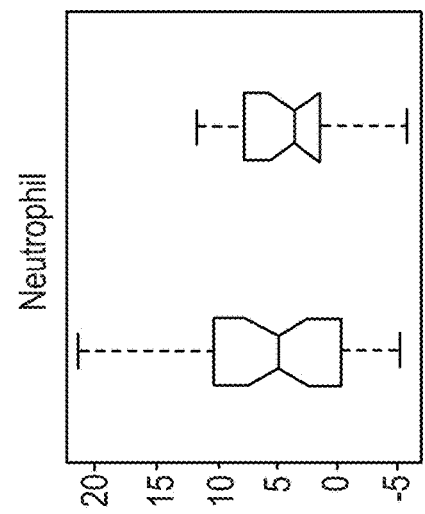
Figure 10B:
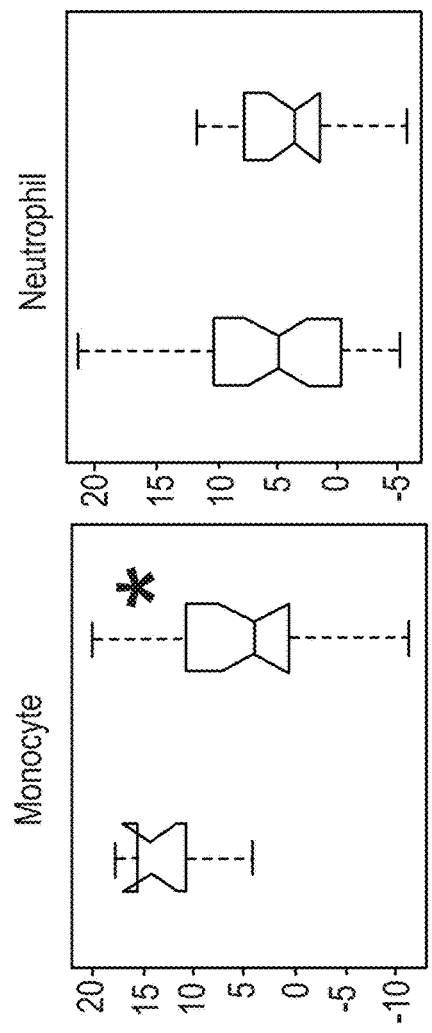
Figure 10C:
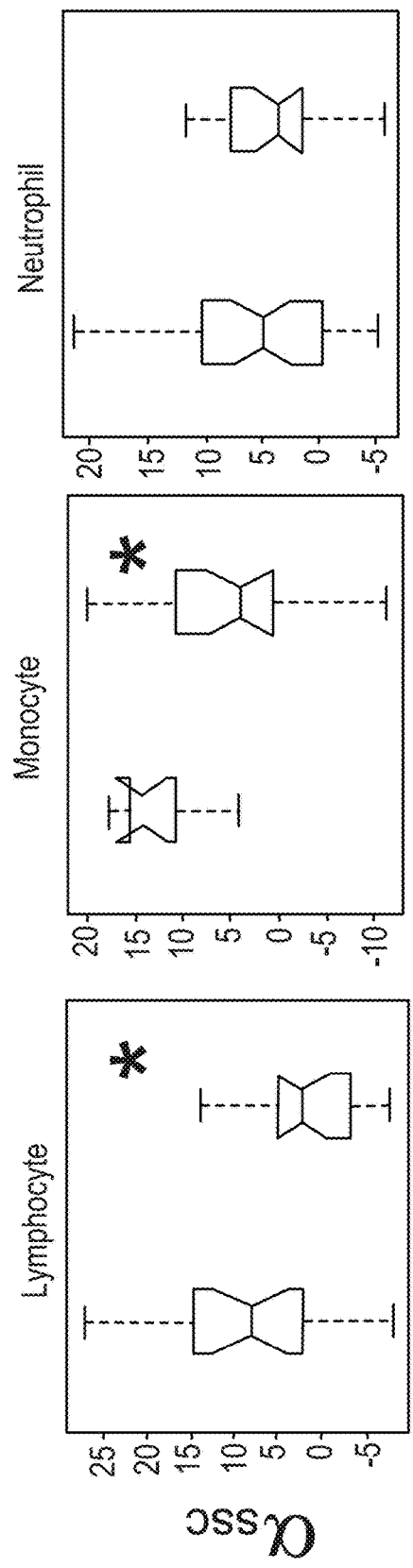
Figure 10D:
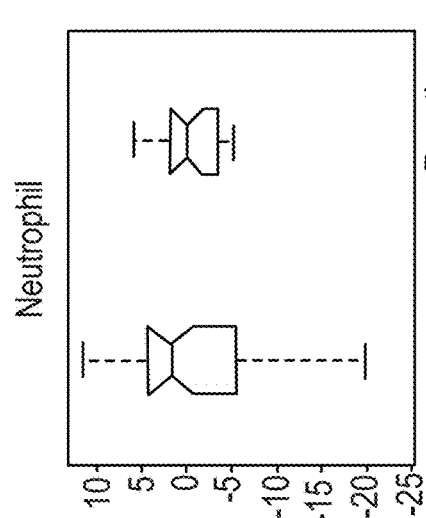
Figure 10E:
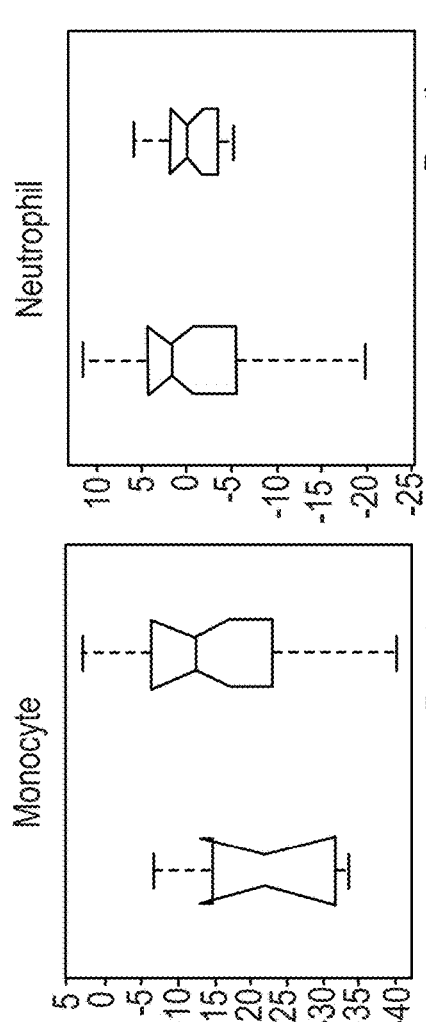
Figure 10F:
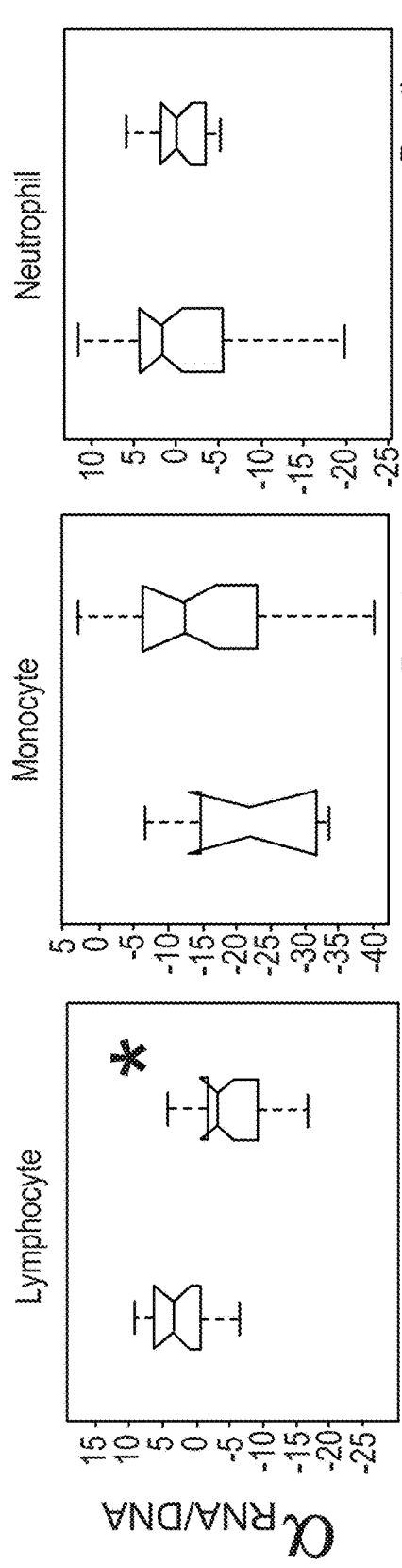

FIGS. 5A-B. (A) Comparison of WBC differentials between the cohorts whose Troponin-T goes up (High), versus those whose Troponin remained normal (Low). LYM, Lymphocytes; MON, Monocytes; NEU, Neutrophils. These patient groups cannot be distinguished based on the tradition WBC differential. (B) Depiction of the drift functions in the mathematical model.

FIGS. 6A-C. Representation of the distribution upon parameter fitting using the mathematical model for the lymphocyte population (Black-Fitted distribution, White-Empirical/measured distribution). For this particular fitting exercise, the sum of square of errors/objective function was 1.56e-4, and the first order optimality condition was 1.11e-4, demonstrating a very good fit of the model to the data. (A) Surface plot showing the fitted distribution, (B) X-Z projection of the surface plot in (A), (C) Y-Z projection of the surface plot in (A).

FIGS. 7A-C. Varying mathematical expressions chosen for the drift with respect to the ALL grid (A) Original piecewise expression, (B) Piecewise Quadratic, (C) Piecewise Linear. The qualitative shapes of these curves is what makes the model informative and not the specific mathematical expression.

FIGS. 8A-H. (A-D) Comparing the model parameters using the different expressions for $\alpha_{ALL}$ (O-Original, L-Linear, Q-Quadratic) from FIGS. 7A-C, and using Equation 5 for $\alpha_{IAS}$. (In each section, the left hand bar depicts the original expression as shown in Equation 4, the middle bar depicts the linear expression as shown in Equation 11, and the right hand bar depicts the quadratic expression as shown in Equation 12). The parameters for the low Tn-T cohort versus the high Tn-T cohort have been compared separately (Low Tn-T depicted by x-axis tick label, L; High Tn-T depicted by x-axis tick label, H). (E-H) Comparing the model parameters using the different expressions for $\alpha_{IAS}$, but using Equation 4 for $\alpha_{ALL}$. (In each section, the left hand bar depicts the original expression as shown in Equation 5, the right hand bar depicts the linear expression as shown in Equation 13). The parameters for the low Tn-T cohort versus the high Tn-T cohort have been compared separately (Low Tn-T depicted by x-axis tick label, L; High Tn-T depicted by x-axis tick label, H). Patient-specific model parameters are determined by the qualitative mechanistic structure of the equations and not the specific mathematical expressions.

FIGS. 9A-L. Comparing the model parameters for patients with no measurements of Tn-T (healthy), normal (low) Tn-T, and high Tn-T for (A-D) Lymphocytes, (E-H) Neutrophils, and (I-L) Monocytes.

(FIG. 10 shows data collected on a Sysmex hematology analyzer.)

FIGS. 10A-L. Parameter estimates for cellular population dynamics of lymphocytes, monocytes, and neutrophils for patients with malignant versus reactive leukocytosis. Five (marked with *) of 12 parameters independently provide statistically significant discrimination (p<0.05) between pilot cases (n=20) and controls (n=22). Parameter distributions are shown as notched boxplots where the central horizontal line shows the median, the box extends from the 25th to the 75th percentile, and the notches show the extent of a 95% confidence interval for the median. Dashed lines show extent of outliers that are no farther from the median than 1.5-times the inter-quartile range. Plus symbols show more extreme outliers.

Figure 11:
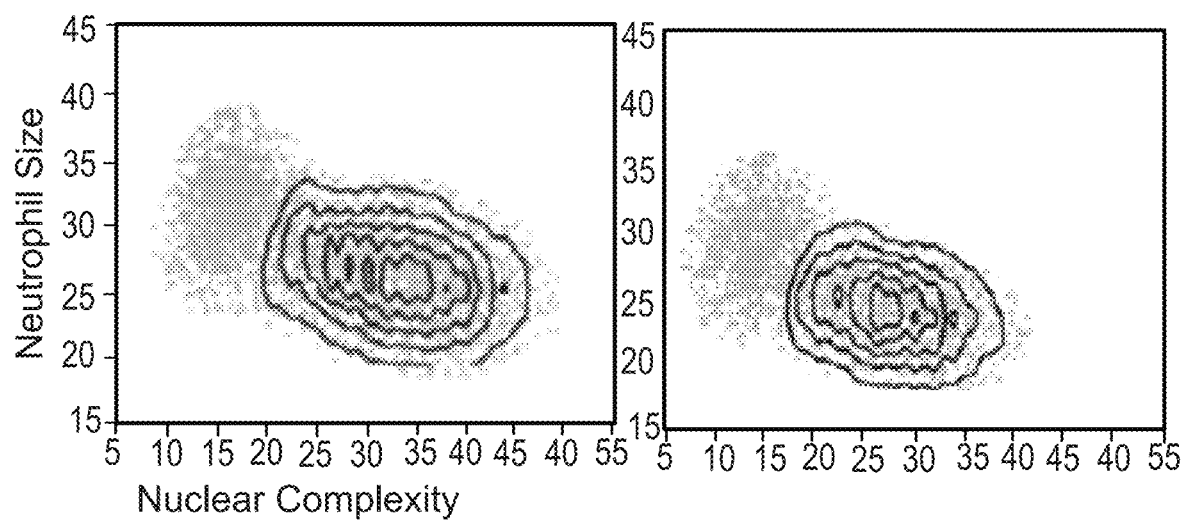
Figure 12:
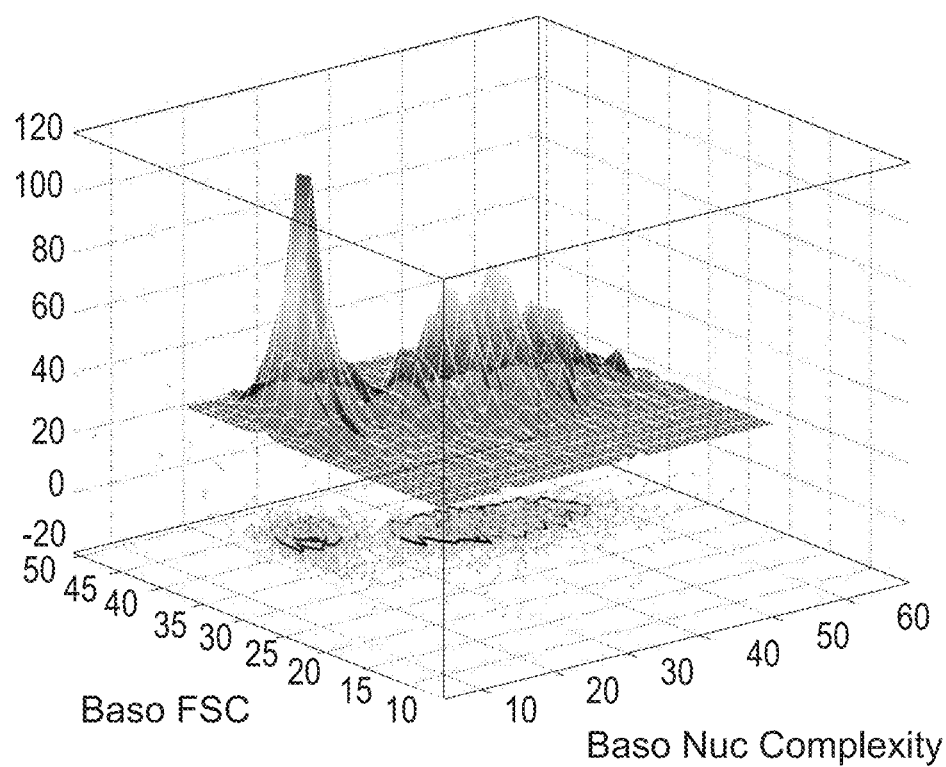
Figure 13:
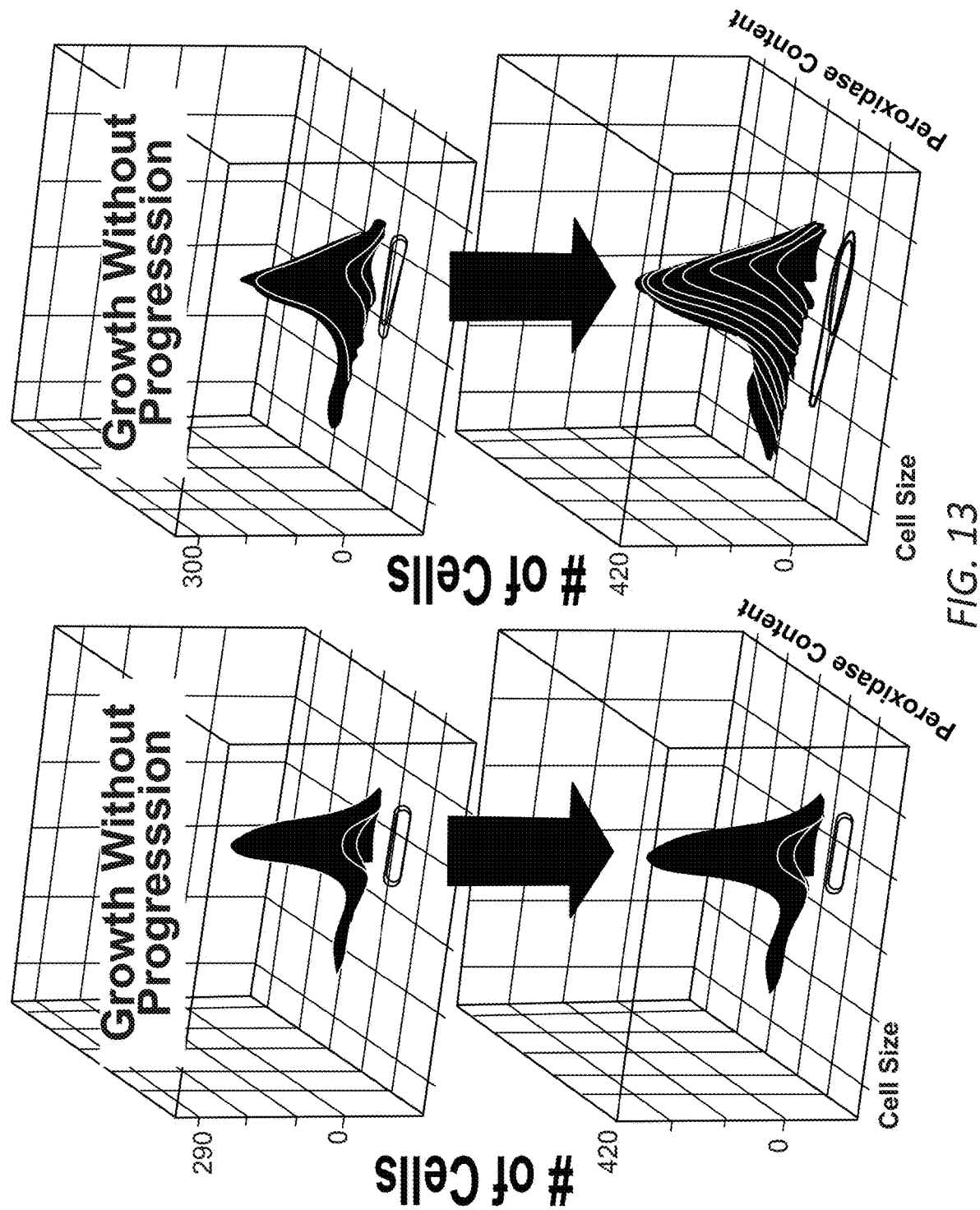

(FIGS. 11-13 show data collected on a Siemens hematology analyzer.)

FIG. 11. Distributions of neutrophil size and complexity for two patients subsequently diagnosed with acute myelogenous leukemia (AML). The left panel is from a patient with very aggressive disease, the right from a patient with slowly progressing disease. Aggressive disease was associated with greater diffusivity in the WBC population dynamics, leading to an increase in the variation (width) in neutrophil nuclear complexity as demonstrated by the wider contour plot in the left panel compared to the right. The pattern was statistically significant in a set of 120 patients with newly diagnosed AML.

FIG. 12. Surface plot of the data in FIG. 11A, with the z-axis showing the number of cells.

FIG. 13. Lymphocyte population dynamics for two patients with chronic lymphocytic leukemia (CLL). The left surface and contour plots show the distributions of lymphocyte size and peroxidase content at an initial (top left) and later (bottom left) time point. This patient's disease was stable as were the lymphocyte population distributions (shape of the surfaces and contours), despite a significant increase in lymphocyte count (z-axis). The right surface and contour plots show a patient with progressing disease whose lymphocyte count increased by the same fraction. Progressive disease was associated with a qualitative change in lymphocyte population dynamics seen as a change in the shapes of the surface and contour plots.

DETAILED DESCRIPTION

Most automated hematology analyzers are sophisticated instruments that measure several single-cell characteristics for tens of thousands of WBCs, RBCs, and platelets. Each routine CBC thus involves hundreds of thousands of single-cell measurements, but clinical decisions are usually based on only a few derived statistics, e.g., a total count of WBCs, RBCs, and platelets. The vast potential of the complete data set collected during each CBC measurement has been well-appreciated, and many previous efforts have been undertaken to extract additional information, for instance by trying to detect early infection by identifying "immature" granulocytes sometime called "band" cells, or guiding stem cell collection by estimating the number of circulating hematopoietic progenitor cells, or providing early detection of some hematologic malignancies by counting the number of WBCs with atypical characteristics. These efforts have had limited impact but hint at the potential for clinical decision support within these large data sets collected during routine CBCs[4]. More recent work has combined these existing high-resolution clinical data sets with semi-mechanistic models of blood cell maturation, activation, and clearance to provide patient-specific estimates of the rates of these cellular processes. The population dynamics of a patient's blood cells often sensitively reflect pathophysiologic states and thus provide insight into physiologic processes and opportunities for earlier and more accurate diagnosis and prognosis[12].

Described herein are dynamic population models using raw CBC measurements for neutrophil, lymphocyte, and monocyte populations. The dynamic population models can be used to estimate changes in the WBC count and population over a period of time. For example, the parameters of the dynamic population models can be indicative of rates of change of the WBC count. While a single measurement of a WBC count accounts for the current number of WBCs, the parameters of the dynamic population models are indicative of changes in the WBC count over time and thus can be used for early diagnosis or treatment of a patient for a condition.

The CBC can be performed on a sample of WBCs from a patient and can provide measurements of morphological properties and intracellular composition (e.g. size, internal complexity, nuclear lobularity, peroxidase content, DNA/RNA content) of each WBC in the sample. Based on the measurements of the properties of each WBC, the models quantify the rates of change in these characteristics for a typical WBC as well as the variation in the rates of change from one cell to the next and for the same cell at different points. These rates of change in single-cell characteristics and the magnitude the variation in these rates of change are associated with changes of each WBC count, e.g., a neutrophil count, a lymphocyte count, or a monocyte count. For instance, young neutrophils are larger on average than mature neutrophils, and an increased rate of production of new neutrophils is thus associated with an increase in the average size of a patient's circulating neutrophil population, and the rate of increase in the average size thus provides an estimate of the rate of increase in the neutrophil count. As another example, cytoplasmic granularity increases during infection, and the rate of increase can be correlated with the intensity of the inflammatory response. The rates of change in the single-WBC characteristics measured by the CBC thus enable quantification of the net effects of cellular production, maturation, activation, and clearance on these three WBC subpopulations. As shown herein, these dynamics are different between healthy and sick patients, even in those whose absolute WBC counts are indistinguishable. As a result, the population dynamics and the rates of change of morphological and compositional attributes of the populations of WBCs can be used to differentiate healthy and sick patients, even those who have similar WBC counts.

To determine the rate of change of the WBC count, a property indicative of a maturity or age of each WBC can be measured. The property can be a morphological characteristic or an optical characteristic that is indicative of an age or maturity or activation state of a WBC. The property can be, for example, a cell size, a cytoplasmic granularity, a morphology, a nuclear morphology, or nuclear granularity. For a given WBC, any of these properties can be an indicator of a current age of the WBC. In this regard, measurements of any one of these properties for each WBC can be used to characterize dynamics of the population of the WBCs.

Model parameters can be estimated for individual patients, e.g., using one or more routine CBCs, e.g., pairs of routine CBCs, e.g., using a standard normal template CBC and a single patient CBC. Values of the model parameters are estimated based on the measurement of the property of each WBC in the sample of WBCs taken from the patient. The clinical relevance of these models is shown in acute coronary syndrome, one of the leading causes of death worldwide, and leukemia/reactive leukocytosis. Inferring a patient's WBC population dynamics improves the risk stratification of patients being evaluated for acute coronary syndrome or the diagnosis of reactive leukocytosis (e.g., infection) versus malignant leukocytosis (e.g., leukemia) using existing routine clinical data.

Measuring WBC Population Dynamics

Many common clinical laboratory hematology analyzers measure single-WBC and single-platelet morphologic characteristics, for instance, analyzers sold by Abbott, Sysmex, Siemens, and Beckman. These devices measure different optical or morphologic characteristics of each WBC in a patient blood sample. These characteristics were selected on the basis of their ability to distinguish WBCs from different lineages and at different levels of maturation and thus can be used to estimate an age, maturity, or activation state of a WBC. For instance, many analyzers include single-WBC optical characteristics with intensities that correlate with the degree of nuclear lobularity, which, in turn, is correlated with the degree of maturation, e.g., the age of the WBC. See, e.g., Bainton et al., Developmental Biology of Neutrophils and Eosinophils, 1969, Ser Haematology 3: 3-43.

Modeling can proceed with the raw device measurements or with the mapping of those device measurements into a standard instrument-neutral set of coordinates (age=$f^1$(raw)) reflecting estimated age and activation. When the raw device measurements are used, then $f^1$ is simply defined as the identify function.

Given a single-cell or single-platelet characteristic, normal magnitude of variation is quantified by analyzing distributions among a healthy cohort. This variation is decomposed into components of drift and diffusion which are included in models of single-cell and single-platelet population dynamics.

Dynamics for each characteristic (raw or mapped) are preferably modeled in the following way. Given a cell or platelet's position along a characteristic coordinate (e.g., side scatter or SSC), established physiologic mechanisms are used to constrain the mathematical form of an equation describing the cell's most likely position along that coordinate at the next point in time as a function of all available current characteristics. For characteristics whose levels increase with time on average, the relation looks like the following.

$$d/dt \, N(f^{-1}(SSC)) = \alpha N(f^{-1}(SSC) - 1, \ldots)$$

where N( ) represents the number or proportion of cells or platelets whose SSC value is the same at time t and whose other characteristics (e.g., forward scatter, RNA/DNA content, peroxidase content, axial light loss, intermediate angle scatter, polarized side scatter, depolarized side scatter, electrical impedance, etc.) are included as necessary. Second-order diffusive terms can be added where appropriate based on known physiology or mechanistic uncertainty.

A similar expression is derived for the number or fraction of cells produced with the same level of SSC: $\gamma N_0(f^{-1}(SSC), \ldots)$. This expression, when positive, contributes to a positive rate of change of the cell count.

A similar expression is derived for the number or fraction of cells cleared from the circulation with the same level of SSC: $\delta N_0(f^{-1}(SSC), \ldots)$. This expression, when positive, contributes to a negative rate of change of the cell count.

These processes can be combined to yield an expected rate of change in the number of cells or platelets with a given set of characteristics:

$$d/dt \, N(f^{-1}(SSC)) = \alpha N(f^{-1}(SSC) - 1) - \beta N(f^{-1}(SSC)) + \gamma N_0(f^{-1}(SSC)) - \delta N(f^{-1}(SSC))$$

The model parameters scaling each contributing process can then be identified for individual patients from their raw complete blood count measurements. These parameters are then used to provide a high-resolution hematologic and immunologic phenotype which can be used to screen patients for common illness and within chronic disease groups to stratify patients for risk. Although the exemplary approach described in the examples below used multiple CBC measurements from the same patient, in other methods a reference level can be used that represents a chosen population, developed using standard statistical methods based on a selected cohort of patients.

Parameters for population dynamics of different cell types or platelets can be combined in composite diagnostic algorithms. For instance, while an increasing neutrophil size or count alone increases the near-term risk of an infection, the combination of an increasing neutrophil count or size and a decreasing lymphocyte count or size (below) may be better correlated with a diagnosis of leukemia.

These methods may be used to make new diagnoses earlier and more accurately than is otherwise possible and may also be used to stratify patients with chronic disease, for instance predicting prognosis for two different patients with chronic lymphocytic leukemia as shown below.

Acute Coronary Syndrome

Acute coronary syndrome is caused by insufficient oxygen supply to the myocardium and involves either a myocardial infarction (MI) or unstable angina[6]. It was hypothesized that the severe ischemia and developing infarction can trigger an immediate and substantial systemic inflammatory response that can be detected in terms of its perturbations of the dynamics of WBCs. Troponin I, C and T (Tn-I, Tn-C, Tn-T) are proteins found in the cardiac muscles, which start leaking and become detectable in the blood, upon necrosis of these cardiac tissues[7-9]. Serum levels of this protein typically increase over a few hours, and peak over several hours and up to a day or two, from the onset of symptoms and are currently the current gold standard for diagnosing MI. In contrast, patients experiencing unstable angina or other pathology not associated with MI will show WBC population dynamics that are unchanged or changed in a qualitatively different manner.

Because serum troponin levels are often normal in patients subsequently diagnosed with MI, consideration of WBC population dynamics can help identify patients with ACS who have initially negative troponin and will most likely be found with an elevated troponin in the next several hours.

As shown herein, patients diagnosed with MI have significantly different WBC dynamics from those who are healthy, even after controlling for absolute WBC count. The present methods can help identify patients being evaluated for MI who are most likely to have an elevated Tn level in the near future and thus receive that diagnosis.

In addition to providing complementary information about a patient's clinical state, this model generates novel hypotheses about the underlying pathophysiological perturbations to WBC population dynamics, which represent the direct pathologic effects of disease, as well as the physiologic response to this pathology. For instance, the median and variance of the lymphocyte $D_{ALL}$ and $\alpha_{IAS}$ parameters are higher in the cohort of patients who go on to have an elevated Tn-T measurement. This finding suggests that the distribution of the volumes of circulating lymphocytes widens for patients developing MI. Lymphocytes are hyperproliferative cells that continue to proliferate upon activation, and this widening of the size distribution could be attributed to the presence of greater numbers of naïve cells, smaller activated cells entering the circulation from the bone marrow or thymus, or larger activated cells undergoing further proliferation[14-16]. Lymphocytes do not generally have a granular and complex cytoplasmic structure, and the finding of an increase in the measured internal complexity of these agranulocytes may reflect activation as consequence of progressing myocardial ischemia. The ALL measurement generally reflects cell size, and the significant difference in $\alpha_{ALL}$ shown in FIG. 3A suggests enrichment of smaller neutrophils in advance of a clinical diagnosis of MI, as compared to patients who remain stable. Smaller neutrophils have been shown to be older[17], and this enrichment may reflect a consumption of younger neutrophils or a state of activation which is associated with a reduction in cell size[18,19]. The modified parameter depicting the lobularity of the neutrophils is consistent with the presence of an increased number of band neutrophils in the circulation, as has been shown before[20,21]. The decreased monocyte $\alpha_{ALL}$ for patients progressing to MI suggests an enrichment in smaller monocytes in the circulation, which could be attributed to accelerated proliferation or maturation[22].

Hematologic Malignancy

Subjects with elevated WBC count (e.g., WBC count>11× $10^3$ cells/ul) ("leukocytosis") are most likely to have an underlying infection ("reactive leukocytosis") or a hematologic malignancy ("malignant leukocytosis"). Because the treatments for these conditions differ greatly, and early intervention can be crucial to outcome, it is important to have a rapid method of making a differential diagnosis. As described herein, five of twelve of the model parameters were different with statistical significance between reactive and malignant leukocytosis, and a cross-validated decision tree classifier using a subset of parameters ($\alpha_{SSC,L}$, $\alpha_{SSC,M}$, $\alpha_{RNA/DNA,L}$, $D_{SSC,L}$, and $D_{SSC,M}$) could distinguish patients who end up with each diagnosis with an accuracy of about 82%. Patient CBC measurements were used to estimate the best-fit parameters for each patient using the model and standard parameter estimation methods. The classifier was then developed using supervised learning techniques to train a decision tree classifier using model parameters that were significantly different for the patients.

A subject diagnosed with an underlying infection can be, e.g., further evaluated to determine the site (i.e., location in the body of the subject) and species of infection and/or treated with an antibiotic regimen. A subject diagnosed with a malignancy can be, e.g., further evaluated (for instance by serum protein electrophoresis, flow cytometry of peripheral blood, other clinical laboratory assay, bone marrow biopsy, or imaging) to determine the specific type of malignancy, and/or treated with standard anti-cancer therapies, e.g., depending on the type of cancer by purine analogs such as fludarabine, alkylating agents such as chlorambucil, monoclonal antibodies such as rituximab, tyrosine kinase inhibitors, or other chemotherapy, targeted molecular therapy, and/or radiation. Malignancies that can be first identified this way include ALL, AML, CLL, CML, multiple myeloma, lymphomas, and solid tumors triggering an overt inflammatory response. The model can help differentiate between these diagnoses and can also help identify more benign or more severe cases of each, for instance FIGS. 11 and 13 show how more benign and more severe cases of AML and CLL can be identified earlier, enabling earlier treatment.

EXAMPLES

The invention is further described in the following examples, which do not limit the scope of the invention described in the claims.

Example 1

White Blood Cell Population Dynamics in Acute Coronary Syndrome

The complete blood count (CBC) is one of the most common clinical tests, integral to the diagnosis, treatment, and monitoring of almost all diseases because it provides a simple high-level assessment of health of the patient's hematologic and immunologic systems by reporting an estimate of the current number of each type of blood cell circulating per unit volume blood. Increases or decreases in the counts if different cell types may indicate anemia, infection, malignancy or more. Most routine CBCs involve high-resolution and high-throughput single-cell measurements of the morphology of tens of thousands of blood cells, providing single-cell details of morphology, protein concentration, or other characteristics. These single-cell characteristics reflect states of maturation, activation, production, destruction and the perturbation of those processes in different disease conditions. If we can infer these states and their rates of change from routine blood counts, we can diagnosis disease earlier and more precisely. Here we develop a mathematical model of white blood cell population dynamics inspired by cellular mechanisms for this purpose. We first show that this model can be useful to distinguish healthy individuals from those are not healthy, and we then show how the model can improve the risk-stratification of patients being evaluated for acute coronary syndrome. This study demonstrates how mechanistic modeling of existing clinical data can realize the vision of precision medicine.

Methods

The following materials and methods were used in the Example below.

Patients and Lab Measurements

We analyzed raw data collected during each patient's first CBC measurement. We then inferred WBC population dynamics, parameterized by drift and diffusion terms for neutrophil, lymphocyte, and monocyte populations. We defined an elevated Troponin measurement to be indicative of an MI[8]. Patients with MI often have elevations in the count of WBCs[10,11], and we therefore controlled for WBC count when comparing cases and controls. A patient with a normal WBC count may be hard to diagnose for the underlying causality of the symptom. This study specifically focused on patients who have a normal WBC count, and are thus hard to be screened based on CBC alone. The patient subsets were chosen conservatively and were limited to those with normal WBC count at the time of the Troponin test. Thus, purely based on the patient's CBC, no distinction could be made pertaining to the underlying causes that trigger the symptoms.

Patient Blood Sample Collection and Characterization

Patient data was accessed under a research protocol approved by the Partners Healthcare Institutional Review Board. All CBC measurements were made by an Abbott Cell-DYN Sapphire automated hematology analyzer (Abbott Diagnostics, Santa Clara, Calif.). The analyzer made several optical measurements, including Axial Light Loss (ALL) representing cell size, Intermediate Angle Scatter (IAS) representing cellular complexity, Polarized Side Scatter (PSS) representing nuclear lobularity, Depolarized Side Scatter (DSS) distinguishing granulocytes (neutrophils and eosinophils), and a fluorescence signal separating nucleated red blood cells, stromal cells and the mononuclear agranulocytes (lymphocytes and monocytes)[23]. It was hypothesized that cellular size and cytoplasmic complexity would provide useful correlates of cellular maturation and activation and therefore the analysis focused on the ALL and IAS measurements. Since lymphocytes and monocytes are morphologically mononuclear, the relevance of nuclear lobularity seemed limited, and hence the PSS measurement was only studied for neutrophils.

The study group (SG) comprises of 1285 patients who had a Troponin-T or Tn-T (Roche Diagnostics, Basel, Switzerland) test ordered at MGH (between June 2012-July 2015). Repeat CBC measurements (after June 2012) were also considered for those patients at the time of a Tn measurement. The healthy cohort, or control group (CG), was obtained from serial measurements of healthy patients (141 patients), who had not had an abnormal CBC index over a couple years, and who had not visited the hospital within 250 days, in order to enrich for patients whose only medical visits were for annual physical examination.

Upon filtering the overall set of patients (SG), we could identify a subset of interest, 'Low Tn-T', containing 91 patients (pairs of blood samples, n=153) who have a low Tn-T measurement (Tn-T<=0.03 ng/mL), while the high Tn-T group (Tn-T>=0.09 ng/mL), 'High Tn-T', contains 80 patients (n=201 separate blood samples). To ensure accurate capture of the dynamical behavior of the population, samples not rendering a good parameter fit (Objective function/sum of square of error, SSE≥0.005 for Lymphocyte and Monocytes, SSE≥0.007 for Neutrophils) were excluded. We finally end up with 102 unique patients and have ensured that they have a normal WBC count (4,000-11,000 cells/μl) at the first time point, and WBC<17,000 at the time of Tn-T being ordered, and have good parameter fits. These two cohorts were also matched based on their WBC count (difference less than $0.5 \times 10^3$ cells/μl). FIG. 5A suggests no significant difference in the WBC differentials between the two cohorts in question, rendering them indistinguishable based on their bulk WBC measurement and differential.

A validation set of 100 patients (Validation Group, or VG) was considered to test the accuracy of classification based on model parameters. Patients who had Tn-T measurements at MGH after August 2015 were considered in this cohort. (FIG. 4C-F)

Mathematical Model

The blood count provides a multivariate distribution of single-cell optical scatter properties that relate to single-cell size, cytoplasmic granularity, nuclear morphology, and other characteristics. The evolution over time of the probability density (P) of these single-cell properties was modeled, and this evolutionary process for each cell population was decomposed into drift (α) and diffusion (D) processes. The Fokker-Planck equation is a partial differential equation that describes this sort of temporal evolution of a probability density function under forces of drift and diffusion. The model presented herein provides a description of the true WBC population dynamics, with resolution limited by the underlying measurements comprising the CBC. This model utilizes known cellular physiology where possible and makes informed assumptions otherwise.

The general Fokker-Planck equation describing the time-based evolution of P under drift (α) and diffusion (D) used was the following:

$$\frac{\partial P_i}{\partial t} = \nabla(P_i \alpha) + \nabla \cdot (D \cdot \nabla P_i) \quad (1)$$

In Equation 1. $P_i$ is the probability density for the single-cell measurements of the $i^{th}$ WBC sub-population (ie neutrophils, lymphocytes, monocytes). α depicts the "velocity" of the drift term, and D depicts the diffusion coefficient. See FIG. 1 for a schematic of an exemplary modeling approach[12]. Using the drift and the diffusion term in the equation, the trajectory of the heterogeneous cellular population was mimicked as it deviated from a healthy state or fluctuated around a healthy state. The birth and death of cells, or more generally, the fluxes in and out of circulation, were implicitly modeled in the drift term of the equation. The intent was to model the probability density of cellular activation, maturation, etc., which can be appropriately captured by the Fokker-Planck equation, while acknowledging the limitations posed by gaps in physiologic knowledge.

The lineage specific master equation can be written as $$\frac{\partial P_i}{\partial t} = \frac{\partial}{\partial x_{ALL}}(\alpha_{ALL,i} P_i) + \frac{\partial}{\partial x_{IAS}}(\alpha_{IAS,i} P_i) + D_{ALL,i}\frac{\partial^2 P_i}{\partial x_{ALL}^2} + D_{IAS,i}\frac{\partial^2 P_i}{\partial x_{IAS}^2} \quad (2)$$

In Equation 2, $P_i$ is the 2-D probability density of the $i^{th}$ WBC subpopulation, $D_{ALL,i}$ and $D_{IAS,i}$ are the diffusive coefficients with respect to the ALL and the IAS dimensions, and $\alpha_{ALL,i}$, $\alpha_{IAS,i}$ are the drift parameters.

Model Details

The morphology (e.g., size and complexity) of individual cells can be utilized as a crude indicator of cell age and activation state, and the distribution of these characteristics can be correlated with many disease processes. There remain unanswered questions regarding the lifecycle of WBCs in general and during heterogeneous pathologic conditions that alter rates of activation, maturation, and apoptosis. Therefore, source terms (e.g. birth and death) were not included in order to avoid making strong assumptions about the rates of production, proliferation, or turnover. Instead, the drift and diffusion terms provided an overall lumped quantification of those processes and their effects on the distribution of cellular characteristics.

The model for the time-based evolution of the distribution of lymphocyte ALL and IAS ($P_{LYM}$) is written in the form of a drift-diffusion or Fokker-Planck equation:

$$\frac{\partial P_{LYM}}{\partial t} = \frac{\partial}{\partial x_{ALL}}(\alpha_{ALL,L} P_{LYM}) + \frac{\partial}{\partial x_{IAS}}(\alpha_{IAS,L} P_{LYM}) + D_{ALL,L}\frac{\partial^2 P_{LYM}}{\partial x_{ALL}^2} + D_{IAS,L}\frac{\partial^2 P_{LYM}}{\partial x_{IAS}^2} \quad (3)$$

The drift terms ($\partial/\partial x_{ALL}$ and $\partial/\partial x_{IAS}$) captured the changes in the median heterogeneity with respect to a morphological attribute, while the diffusion terms ($\partial^2/\partial x_{ALL}^2$ and $\partial^2/\partial x_{IAS}^2$) tracked the changes in the variance of the distribution. A change in the central tendency or median was generally hypothesized to be caused by a change in the distribution of ages or activation states in the circulating population. In Equation 3, $P_{LYM}$ is the 2-D probability density of the lymphocyte population, $D_{ALL,L}$ and $D_{IAS,L}$ are the diffusive coefficients with respect to the ALL and the IAS dimensions.

$\mu_{Pend,IAS}$ and $\mu_{Pend,ALL}$ (see below) represent the median of the IAS and ALL distribution of the final probability density (target distribution used for the fitting) and $\alpha_1$, $\alpha_2$ are the fitted drift parameters. The drift in terms of the ALL grid (FIG. 5B) is expressed as $$\alpha_{ALL} = \alpha_1 \begin{cases} \dfrac{x_{ALL}}{\mu_{Pend,ALL}}, & \text{when } x_{ALL} < \mu_{Pend,ALL} \\ \dfrac{\mu_{Pend,ALL}}{x_{ALL}}, & \text{when } x_{ALL} \geq \mu_{Pend,ALL} \end{cases} \quad (4)$$

and, the drift with respect to the IAS grid is expressed as $$\alpha_{IAS} = \alpha_2 \begin{cases} 1 - 2\dfrac{x_{IAS}/\mu_{Pend,IAS}}{1 + x_{IAS}/\mu_{Pend,IAS}}, & \text{when } x_{IAS} < \mu_{Pend,IAS} \\ 2\dfrac{x_{IAS}/\mu_{Pend,IAS}}{1 + x_{IAS}/\mu_{Pend,IAS}}, & \text{when } x_{IAS} \geq \mu_{Pend,IAS} \end{cases} \quad (5)$$

The growth rate of individual lymphocytes as a function of cellular age or size is unclear and difficult to measure. Some previous investigators have found evidence that the growth rate of lymphoblasts is proportional to volume up to a point and then declines roughly linearly with increasing size[24]. ALL dynamics were represented in a qualitatively compatible way. The growth rate was assumed to increase linearly up to the median of the final ALL distribution after which it decreases. The growth rate at zero volume is zero, and goes up to a maximum value of $\alpha_1$.

It was hypothesized that an important determinant of the cytoplasmic complexity and granularity of cells was cellular responses to activation signals. Therefore, the typical rate of change was modeled as initially very slow and increasing quickly following a signal before stabilizing at a poised level. Michaelis-Menten kinetics are a standard way to model this sort of signaling response, as shown in Equation 5.

The population dynamics of neutrophil and monocyte populations were modeled similarly.

$$\frac{\partial P_{MON}}{\partial t} = \frac{\partial}{\partial x_{ALL}} (\alpha_{ALL,M} P_{MON}) + \quad (6)$$

$$\frac{\partial}{\partial x_{IAS}} (\alpha_{IAS,M} P_{MON}) + D_{ALL,M} \frac{\partial^2 P_{MON}}{\partial x_{ALL}^2} + D_{IAS,M} \frac{\partial^2 P_{MON}}{\partial x_{IAS}^2}$$

$$\frac{\partial P_{NEU}}{\partial t} = \frac{\partial}{\partial x_{ALL}} (\alpha_{ALL,N} P_{NEU}) + \quad (7)$$

$$\frac{\partial}{\partial x_{IAS}} (\alpha_{IAS,N} P_{NEU}) + D_{ALL,N} \frac{\partial^2 P_{NEU}}{\partial x_{ALL}^2} + D_{IAS,N} \frac{\partial^2 P_{NEU}}{\partial x_{IAS}^2}$$

$P_{MON}$ and $P_{NEU}$ are the 2-D probability distributions of ALL and IAS for the monocyte and neutrophil subpopulations. The drift[25,26] and diffusion terms are similar to the lymphocyte model (Equations 4, 5).

Because neutrophils have much more heterogeneous nuclear morphology, a model for the population dynamics of neutrophil nuclear morphology was included as well. Previous investigators have demonstrated that neutrophil nuclear morphology is altered in response to disease, in particular the fraction of neutrophils with band or segmented nucleus morphology has been shown to increase in states of inflammation such as neonatal sepsis[27]. The lobularity of the nucleus is reflected in the Polarized Side Scatter (PSS) measurement. The bottom 2.5 percentile of PSS values for the neutrophils in each sample was calculated to distinguish low lobularity (as seen in band neutrophils) from high lobularity (fully segmented neutrophils). The size of fraction of neutrophils that have a PSS value lower than this threshold was modeled and was hypothesized to reflect that reflect the fraction of immature neutrophils in the circulation. This threshold ($PSS^{th}$=1e4) was chosen as the point depicting the upper quartile of the bounding point separating the $2.5^{th}$ percentile of PSS for neutrophils in all samples. The fractions are compared at the patient's healthy state ($frac_1$), versus at the time point of interest ($frac_2$), and a modified parameter is obtained as $$K_{PSS} = frac_2 (frac_2 - frac_1) \quad (8)$$

The model quantified the deviation from the healthy state for the particular patient in terms of the fraction of neutrophils with significantly reduced lobularity.

Numerical Solution

The Fokker-Planck equation presented in the previous section was solved numerically using the finite-difference method. Upon discretization of the equation in the spatial coordinates, an ordinary differential equation (ODE) was obtained which can be solved using explicit solution techniques. The resulting discretized ODE can be written as $$\frac{dP_{LYM_{i,j}}}{dt} = \alpha_{ALL} \frac{P_{LYM_{i,j}} - P_{LYM_{i-1,j}}}{\Delta x_{ALL}} + \quad (9)$$

$$\alpha_{IAS} \frac{P_{LYM_{i,j}} - P_{LYM_{i,j-1}}}{\Delta x_{IAS}} + D_{ALL} \frac{P_{LYM_{i+1,j}} - 2P_{LYM_{i,j}} - P_{LYM_{i-1,j}}}{\Delta x_{ALL}^2} +$$

$$D_{IAS} \frac{P_{LYM_{i,j+1}} - 2P_{LYM_{i,j}} - P_{LYM_{i,j-1}}}{\Delta x_{IAS}^2}$$

For the lymphocytes, the ALL grid was discretized into 40 bins, and the probability density in the $i^{th}$ ALL bin was described using the first subscript in Equation 9. The IAS grid was also discretized into 40 bins, and the probability density in the $j^{th}$ IAS bin was denoted by the second subscript. The neutrophil model was solved by discretizing the ALL grid into 60 bins, and the IAS grid into 40 bins. Similarly, discretizing the ALL grid into 30 bins, and the IAS grid into 35 bins solved the monocyte model. Discretization strategies were chosen based on the typical range and variation for these measurements in the different subpopulations. The resulting ODE was solved using the variable-step, variable-order (VSVO) solver by employing the ode15s function within MATLAB 2015b (Mathworks®, Natick, Mass., USA). The ALL and IAS grids are normalized in order to span between 0 and 1. The upper and lower bounds for normalizing the ALL grid were 5×10e2 and 3×10e4, while the bounds for the IAS grid were 5×10e2 and 2.5×10e4 respectively. These bounds were chosen by analyzing the maximum and minimum values that typically occur in the WBC measurements (across all the datasets). The model was solved for an arbitrary time point (t=0.5) for all the blood samples in order to normalize parameters as a function of spatial and time coordinates.

Parameter Estimation

The Fokker-Planck equation (Equation 2) was solved iteratively to obtain optimal parameters that started with the initial measured cellular distribution for the patient and evolve according to the equation to match the final measured distribution of the cellular population. The end point reached according to Equation 2 was compared with the patient's actual measured distribution, and the difference was minimized. The error, or objective function (Obj), is defined as follows:

$$Obj = \sum_i \sum_j \left( P_{LYM_{i,j-t_{end}}} - P_{LYM_{i,j,oncasure}} \right)^2 \quad (10)$$

The optimization problem was solved using the Nelder-Mead simplex method (fminsearch using MATLAB), followed by employing the gradient-based Levenberg-Marquardt equation (fminunc using MATLAB). In order to ensure the robustness of the optimization results, 10 different starting points for the optimization were picked in parameter space using the Latin-Hypercube sampling method. The final accepted parameter set was selected from the list of ten optimization results (using the different starting points) based on both the objective function (smallest value) and the first order optimality condition from the gradient-based optimization algorithm (smallest value).

Assessing the Robustness of this Framework:

The expression describing the drift relative to the ALL grid shown in Equation 4 was developed to be consistent with what is known about the biological processes of cellular production, maturation, activation and clearance.

Given the substantial uncertainty in the details of these processes, the precise expression in Equation 4 is an estimate of the true biological process. The precise mathematical form of that expression is not important, but the qualitative biological features it represents are. In order to increase confidence that the results depended on these qualitative features and not the precise and arbitrary functional forms, alternative expressions were developed that differed in their mathematical form but retained consistency with the qualitative basis. The drift in the ALL dimension can alternatively be quantified like the following:

$$\alpha'_{ALL} = \alpha'_1 \begin{cases} \left(\dfrac{x_{ALL}}{\mu_{P_{end,ALL}}}\right)^2, & \text{when } x_{ALL} < \mu_{P_{end,ALL}} \\ \left(\dfrac{x_{ALL} - \mu_{P_{end,ALL}}}{\mu_{P_{end,ALL}}}\right)^2, & \text{when } x_{ALL} \geq \mu_{P_{end,ALL}} \end{cases} \quad (11)$$

or $$\alpha''_{ALL} = \alpha''_1 \begin{cases} \dfrac{x_{ALL}}{\mu_{P_{end,ALL}}}, & \text{when } x_{ALL} < \mu_{P_{end,ALL}} \\ \dfrac{x_{ALL} - \mu_{P_{end,ALL}}}{\mu_{P_{end,ALL}}}, & \text{when } x_{ALL} \geq \mu_{P_{end,ALL}} \end{cases} \quad (12)$$

Alternate expressions have also been considered for the IAS drift term:

$$\alpha'_{IAS} = \alpha'_2 \begin{cases} \min\left(1, \max\left(0, \dfrac{x_{IAS} - \mu_{P_{end,IAS}}}{\mu_{P_{end,IAS}}}\right)\right), & \text{when } x_{IAS} > \mu_{P_{end,IAS}} \\ \min\left(1, \max\left(0, \dfrac{\mu_{P_{end,IAS}} - x_{IAS}}{\mu_{P_{end,IAS}}}\right)\right), & \text{when } x_{IAS} \geq \mu_{P_{end,IAS}} \end{cases} \quad (13)$$

FIGS. 8A-H confirm the robustness of the model to variation in the precise mathematical details while retaining qualitative consistency with the coarsely defined biological mechanisms. Different expressions for the drift term did not provide significantly different parameters, and did not alter the results.

Comparing parameter values for patients who did not have any cardiac symptoms (lack of a Tn-T measurement is assumed to be associated with a healthy state of the patient, provided none of the CBC parameters are abnormal as well), potential cardiac symptoms but not acute myocardial infarction or AMI (low Tn-T), and cardiac discomfort caused by AMI (high Tn-T) also yields statistically significant differences, as shown in FIG. 9A-L.

Results

The effect of an acute disease process on WBC population dynamics was assessed by comparing model parameters for healthy individuals to parameters for patients with elevated troponin levels, the gold standard marker for MI[13]. The absolute WBC count is a well-established marker of disease in general and MI in particular, and in order to assess the effect of myocardial ischemia and infarction on WBC population dynamics independent of changes in WBC count, cases and were matched to controls to ensure that each case-control pair differed in total WBC count by less than $0.5 \times 10^3$ cells/µl at the time of each CBC used to infer population dynamics. The CBC pairs for each case and control were thus indistinguishable based on the WBC count, but FIGS. 2A-E show that 6 of 13 model parameters differed between the two groups with statistical significance.

This clear difference in dynamic model parameters shows that MI significantly perturbs WBC population dynamics independent of WBC count and that this perturbation was detectable even with this coarse model of WBC population dynamics based on routinely available CBC raw data. See equations 3, 6, and 7 for more detail. The diffusion coefficient in ALL (or size) was significantly different for all three WBC subtypes, indicating a difference in the composition of the cellular sizes for the case versus control. In addition to that, all the parameters were significantly different (between the cases and controls) for the monocyte population. This comparison comprised healthy ("Control") patients versus patients visiting the hospital with symptoms indicating chest discomfort, however not everyone in the "Study" group had AMI, but all were acutely ill.

It was hypothesized that WBC population dynamics would reflect some of the earliest effects and responses to the myocardial ischemia preceding MI. At the time of symptom presentation for the Study patients in FIGS. 2A-E, these pathologic effects and physiologic responses were well underway and, even after matching patients for absolute WBC counts, clearly distinguished the typical patient with MI from that without. Assuming that these perturbations to WBC population dynamics occur very early, this model can be used to identify some of the patients with MI before the myocardial ischemia has progressed to the point where significant myocardial cell death has occurred, with subsequent leakage of Tn into the bloodstream. This hypothesis was tested by comparing WBC population dynamics for patients at the time of an initially negative Tn, some of whom maintained a stably negative Tn, and others who progressed to an elevated Tn and a diagnosis of MI. Again, patients were matched by absolute WBC count to focus on differences in WBC dynamics that are independent of WBC count. FIGS. 3A-F show that 5 of 13 parameters were different between these two groups with statistical significance.

The parameters distinguishing the two groups with statistical significance were lymphocyte $D_{ALL}$, $\alpha_{IAS}$; neutrophil $\alpha_{ALL}$, $K_{PSS}$; and monocyte $D_{ALL}$. The patients whose Tn-T went up eventually (indicating AMI), had a higher $D_{ALL}$ suggesting a wider size distribution. The drift with respect to IAS was increased in the high Tn cohort, suggesting a higher fraction of cells with greater internal complexity. $\alpha_{ALL}$ was reduced in neutrophils, suggesting smaller cells. Earlier identification of patients whose Tn is likely to become elevated would enable earlier intervention and possibly improved outcomes for these patients. To assess the utility of this approach for assisting in the risk-stratification of ACS patients, a five-fold cross-validated decision tree classifier was built with the significant model parameters (lymphocyte $D_{ALL}$, $\alpha_{IAS}$; neutrophil $\alpha_{ALL}$ and $K_{PSS}$; and monocyte $\alpha_{ALL}$ and $D_{IAS}$) and the data from the patients shown in FIGS. 3A-F (training set). An independent set of patients with negative Tn levels was then identified, and the accuracy of the classifier assessed when predicting which of those patients would eventually have an elevated Tn level in the subsequent 48 hours. FIGS. 4A-D show the receiver operating characteristic (ROC) curves and confusion matrices for the training set and validation sets. The classifier was developed with a training set, and the classifier thus provided a similar AUC for both data sets as expected when cross-validation was used.

Example 2

White Blood Cell Population Dynamics in Reactive and Malignant Leukocytosis

The present methods were also used to distinguish subjects with reactive versus malignant leukocytosis. A retrospective study was performed on samples from 250 leukemia cases and about 350 non-leukemia cases.

Reactive leukocytosis cases were defined based upon a CBC with all of the following criteria: CBC showed an elevated WBC count (>11e3/ul) but <20e3/ul; the patient had no elevated WBC counts in 12 months prior to CBC; the patient had a positive culture (blood, urine, or sputum) within +/−7 days from the CBC; the patient had no cancer diagnosis in the 6 months following the CBC.

Malignant leukocytosis cases were defined based on CBC all of the following criteria: CBC showed an elevated WBC count but <20e3 ul; the patient had no elevated WBC counts in the 12 months prior to CBC; the patient had NO positive culture (blood, urine, or sputum) within +/−30 days from the CBC; the patient had a new diagnosis of ALL, AML, CML, or CLL in the 6 months following the CBC. These measurements were performed using the Sysmex XE-5000 instrument, which utilizes the optical measurements defined by the side scatter and the RNA/DNA fluorescence stain to categorize the various cellular subtypes in the WBC population. We assume that the nuclear size depicted by the RNA/DNA information is similar to the cellular size, owing to the large nucleus and almost absent cytoplasmic space characteristic of lymphocytes As above, a Fokker-Planck based phenomenological model was used for each lineage:

$$\frac{\partial P_{LYM}}{\partial t} = \frac{\partial}{\partial x_{SSC}}(\alpha_{SSC,L}P_{LYM}) +$$

$$\frac{\partial}{\partial x_{DNA/RNA}}(\alpha_{DNA/RNA,L}P_{LYM}) + D_{SSC,L}\frac{\partial^2 P_{LYM}}{\partial x_{SSC}^2} + D_{DNA/RNA,L}\frac{\partial^2 P_{LYM}}{\partial x_{DNA/RNA}^2},$$

$$\alpha_{SSC,L} = \alpha_{2,L}\begin{cases} 1 - 2\dfrac{\frac{x_{SSC}}{\mu_{P_{end,SSC,L}}}}{1 + \frac{x_{SSC}}{\mu_{P_{end,SSC,L}}}}, & \text{when } x_{SSC} < \mu_{P_{end,SSC,L}} \\ \dfrac{x_{SSC} - \mu_{P_{end,SSC,L}}}{\mu_{P_{end,SSC,L}}} \\ 2\dfrac{\frac{\mu_{P_{end,SSC,L}}}{x_{SSC} - \mu_{P_{end,SSC,L}}}}{1 + \frac{\mu_{P_{end,SSC,L}}}{x_{SSC} - \mu_{P_{end,SSC,L}}}}, & \text{when } x_{SSC} \geq \mu_{P_{end,SSC,L}} \end{cases}, \text{ and}$$

$$\alpha_{RNA/DNA,L} = \alpha_{1,L}\begin{cases} \dfrac{x_{RNA/DNA}}{\mu_{P_{end,RNA/DNA,L}}}, & \text{when } x_{RNA/DNA} < \mu_{P_{end,RNA/DNA,L}} \\ 2\dfrac{\mu_{P_{end,RNA/DNA,L}}}{x_{RNA/DNA}}, & \text{when } x_{RNA/DNA} \geq \mu_{P_{end,RNA/DNA,L}} \end{cases}.$$

The distribution for lymphocyte morphological attributes at an earlier time point measurement for the patient was considered as initial conditions of the PDE. Following the trajectory described in the PDE, the distribution was fit at the later time point to obtain "optimal" parameters.

As shown in FIGS. 10A-L, Kruskal-Wallis tests confirm significantly different parameters for the two cohorts, which can then be utilized to develop a multivariate classifier with additional patient data. A cross-validated decision tree classifier was developed with four-fold cross-validation and had an overall accuracy of about 82%. Discrimination efficiency can be improved when (i) the model structure is optimized for use with the Sysmex optical data, and (ii) a multivariate discriminant is carefully developed.

Example 3

Exemplary Diagnostic Scenarios

The following provide exemplary diagnostic scenarios using methods described herein.

(1) An apparently healthy patient at an outpatient visit has a WBC count of 8. WBC population dynamics modeling shows the estimated neutrophil birth rate is abnormally high, suggesting an acute subclinical infection or other process. The patient can be scheduled for a more detailed focused physical exam in the short term, or a urine culture, sputum culture, or throat swab can be performed in the near term.

(2) A patient hospitalized for exacerbation of congestive heart failure has been stabilized and is preparing for discharge. WBC population dynamics modeling shows an abnormally high lymphocyte birth rate suggesting an acute subclinical infection that greatly increases that patient's chances of being rehospitalized after discharge. The patient's discharge can be delayed by 24 hours for extra monitoring.

(3) A patient with a low platelet count can undergo modeling of platelet population dynamics to help distinguish between consumptive and productive causes or response to treatment.

REFERENCES

1. Statland, B. E., Winkel, P., Harris, S. C., Burdsall, M. J. & Saunders, A. M. Evaluation of Biologic Sources of Variation of Leukocyte Counts and Other Hematologic Quantities Using Very Precise Automated Analyzers. Am. J. Clin. Pathol. 69, 48-54 (1978).
2. Horne, B. D. et al. Which White Blood Cell Subtypes Predict Increased Cardiovascular Risk? J. Am. Coll. Cardiol. 45, 1638-1643 (2005).
3. Tamhane, U. U. et al. Association Between Admission Neutrophil to Lymphocyte Ratio and Outcomes in Patients With Acute Coronary Syndrome. Am. J. Cardiol. 102, 653-657 (2008).
4. Gijsberts, C. M. et al. Hematological Parameters Improve Prediction of Mortality and Secondary Adverse Events in Coronary Angiography Patients: A Longitudinal Cohort Study. Medicine (Baltimore). 94, e1992 (2015).
5. Menezes, A. A., Vilardi, R. F., Arkin, A. P. & Cohen, M. J. Targeted clinical control of trauma patient coagulation through a thrombin dynamics model. Sci. Transl. Med. 9, (2017).
6. Kochanek, K. D., Murphy, S. L., Xu, J. Q. & Arias, E. Mortality in the United States, 2013. NCHS data brief, no 178. Hyattsville, Md.: National Center for Health Statistics (2014).
7. Wilkinson, J. M. & Grand, R. J. A. Comparison of amino acid sequence of troponin I from different striated muscles. Nature 271, 31-35 (1978).
8. Adams, J. E. et al. Cardiac troponin I. A marker with high specificity for cardiac injury. Circulation 88, 101-106 (1993).
9. Apple, F. S. & Collinson, P. O. Analytical Characteristics of High-Sensitivity Cardiac Troponin Assays. Clin. Chem. 58, 54-61 (2011).
10. Koren-Morag, N., Tanne, D. & Goldbourt, U. White blood cell count and the incidence of ischemic stroke in coronary heart disease patients. Am. J. Med. 118, 1004-1009 (2005).
11. Menon, V. et al. Leukocytosis and adverse hospital outcomes after acute myocardial infarction. Am. J. Cardiol. 92, 368-372 (2003).
12. Higgins, J. M. & Mahadevan, L. Physiological and pathological population dynamics of circulating human red blood cells. Proc. Natl. Acad. Sci. 107, 20587-20592 (2010).

13. Daubert, M. A. & Jeremias, A. The utility of troponin measurement to detect myocardial infarction: review of the current findings. Vasc. Health Risk Manag. 6, 691-699 (2010).
14. Thompson, C. B. et al. Size-dependent B lymphocyte subpopulations: relationship of cell volume to surface phenotype, cell cycle, proliferative response, and requirements for antibody production to TNP-Ficoll and TNP-BA. J. Immunol. 133, 2333-2342 (1984).
15. Carstairs, K. THE HUMAN SMALL LYMPHOCYTE: ITS POSSIBLE PLURIPOTENTIAL QUALITY. Lancet 279, 829-832 (1962).
16. Mackay, C. R. Homing of naive, memory and effector lymphocytes. Curr. Opin. Immunol. 5, 423-427 (1993).
17. Casanova-Acebes, M. et al. Rhythmic Modulation of the Hematopoietic Niche through Neutrophil Clearance. Cell 153, 1025-1035 (2017).
18. Hoffstein, S. T., Friedman, R. S. & Weissmann, G. Degranulation, membrane addition, and shape change during chemotactic factor-induced aggregation of human neutrophils. J. Cell Biol. 95, 234-241 (1982).
19. Athens, J. W. et al. Leukokinetic Studies. IV. The Total Blood, Circulating And Marginal Granulocyte Pools And The Granulocyte Turnover Rate In Normal Subjects. J. Clin. Invest. 40, 989-995 (1961).
20. Madjid, M., Awan, I., Willerson, J. T. & Casscells, S. W. Leukocyte count and coronary heart disease. J. Am. Coll. Cardiol. 44, 1945-1956 (2004).
21. Kawaguchi, H. et al. Band neutrophil count and the presence and severity of coronary atherosclerosis. Am. Heart J. 132, 9-12 (1996).
22. Wang, S. Y., Mak, K. L., Chen, L. Y., Chou, M. P. & Ho, C. K. Heterogeneity of human blood monocyte: two subpopulations with different sizes, phenotypes and functions. Immunology 77, 298-303 (1992).
23. De Smet, D. et al. Use of the Cell-Dyn Sapphire Hematology Analyzer for Automated Counting of Blood Cells in Body Fluids. Am. J. Clin. Pathol. 133, 291-299 (2010).
24. Tzur, A., Kafri, R., LeBleu, V. S., Lahav, G. & Kirschner, M. W. Cell Growth and Size Homeostasis in Proliferating Animal Cells. Science (80-.). 325, 167-171 (2009).
25. Neumann, F. R. & Nurse, P. Nuclear size control in fission yeast. J. Cell Biol. 179, 593-600 (2007).
26. Webster, M., Witkin, K. L. & Cohen-Fix, O. Sizing up the nucleus: nuclear shape, size and nuclear-envelope assembly. J. Cell Sci. 122, 1477-1486 (2009).
27. Cornbleet, P. J. Clinical utility of the band count. Clin. Lab. Med. 22, 101-136 (2002).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A system comprising a processing device, and one or more computer-readable non-transitory media storing instructions that are executable by the processing device, and upon execution cause the processing device to perform operations comprising:

estimating a value of a parameter indicative of white blood cell (WBC) population dynamics of a patient based on data indicative of a property value of each WBC in a sample of white blood cells (WBCs) of the patient, the property value of a WBC being indicative of an age of the WBC; and providing information for treatment or diagnosis of a condition of the patient associated with an inflammatory or immune system response based on the parameter.

2. The system of claim 1, wherein the WBCs comprise cells selected from the group consisting of neutrophils, lymphocytes, and monocytes.

3. The system of claim 1, wherein the operations further comprise receiving data indicative of a complete blood count of the patient, the data indicative of the complete blood count being indicative of the property value of each WBC.

4. The system of claim 1, wherein the property value of the parameter is estimated based on data indicative of a predefined normalized property value of WBCs.

5. The system of claim 1, wherein the operations further comprise:

receiving data indicative of a first complete blood count of the patient in which the property value of each WBC in a first sample of WBCs is measured, and receiving data indicative of a second complete blood count of the patient in which the property value of each WBC in a second sample of WBCs is measured, wherein the value of the parameter is estimated based on the data indicative of the first complete blood count and the data indicative of the second complete blood count.

6. The system of claim 1, wherein the operations further comprise:

receiving data indicative of a normal template or ensemble of normal complete blood counts in which the property value of each WBC in a first sample of WBCs is measured, and receiving data indicative of a second complete blood count of the patient in which the property value of each WBC in a second sample of WBCs is measured, wherein the value of the parameter is estimated based on the data indicative of the normal template or ensemble of normal complete blood counts and the data indicative of the second complete blood count.

7. The system of claim 1, wherein the property value is indicative of a property of each WBC selected from the group consisting of cell size, cytoplasmic granularity, morphology, nuclear morphology, and nuclear granularity.

8. The system of claim 1, wherein receiving the data indicative of the property value of each WBC comprises receiving data indicative of axial light loss measurements of the sample of WBCs, intermediate light loss measurements of the sample of WBCs, or polarized side scatter measurements of the sample of WBCs.

9. The system of claim 1, wherein the parameter indicative of the WBC population dynamics of the patient is indicative of a drift or a diffusion of the WBC population dynamics.

10. The system of claim 9, wherein the parameter is selected from the group consisting of $\alpha_{ALL}$, $D_{ALL}$, $\alpha_{IAS}$, $D_{IAS}$, $K_{PSS}$, $\alpha_{SSC,L}$, $\alpha_{SSC,M}$, $\alpha_{RNA/DNA,L}$, $D_{SSC,L}$, $D_{SSC,M}$, and $D_{RBA/DNA,L}$.

11. The system of claim 1, wherein the condition is selected from the group consisting of a hematological malignancy, acute coronary syndrome, urinary tract infection, and an autoimmune disease.

12. The system of claim 1, wherein providing information for treatment or diagnosis of a condition of the patient associated with an inflammatory immune system response based on the parameter comprises providing information for treatment or differential diagnosis of reactive leukocytosis and malignant leukocytosis.

13. The system of claim 1, wherein a troponin level of the patient is within the normal range, and or a WBC count is within normal range.

14. The system of claim 1, wherein the data comprises optical, fluorescence, or impedance single-cell measurements from a complete blood count.

15. The system of claim 1, wherein the data is indicative of a morphological property or intracellular composition of each WBC in the sample.

16. The system of claim 15, wherein the data is indicative of cell size, internal complexity, nuclear lobularity, peroxidase content, or DNA/RNA content of each WBC in the sample.

17. The system of claim 1, wherein the data comprise one or more of Axial Light Loss (ALL) representing cell size; Intermediate Angle Scatter (IAS) representing cellular complexity; Polarized Side Scatter (PSS) representing nuclear lobularity; Depolarized Side Scatter (DSS) distinguishing granulocytes (neutrophils and eosinophils); and a fluorescence signal separating nucleated red blood cells, stromal cells and the mononuclear agranulocytes (lymphocytes and monocytes).

18. The system of claim 17, further comprising comparing the one or more values to a reference value.

19. The system of claim 18, wherein the reference value represents an identified cohort of subjects, or a value determined at an earlier or later point in time in the same subject.

20. A method comprising:
estimating a value of a parameter indicative of white blood cell (WBC) population dynamics of a patient based on data indicative of a property value of each WBC in a sample of white blood cells (WBCs) of the patient, the property value of a WBC being indicative of an age of the WBC; and
providing information for treatment or diagnosis of a condition of the patient associated with an inflammatory or immune system response based on the parameter.

* * * * *

UNITED STATES PATENT AND TRADEMARK OFFICE
CERTIFICATE OF CORRECTION

| | | |
|---|---|---|
| PATENT NO. | : 11,885,733 B2 | Page 1 of 1 |
| APPLICATION NO. | : 17/687270 | |
| DATED | : January 30, 2024 | |
| INVENTOR(S) | : John M. Higgins and Anwesha Chaudhury | |

It is certified that error appears in the above-identified patent and that said Letters Patent is hereby corrected as shown below:

In the Claims

In Column 23, Line 6, Claim 13, delete "and or" and insert -- and/or --

Signed and Sealed this
Eighteenth Day of February, 2025

Coke Morgan Stewart
*Acting Director of the United States Patent and Trademark Office*